Figure 1C:
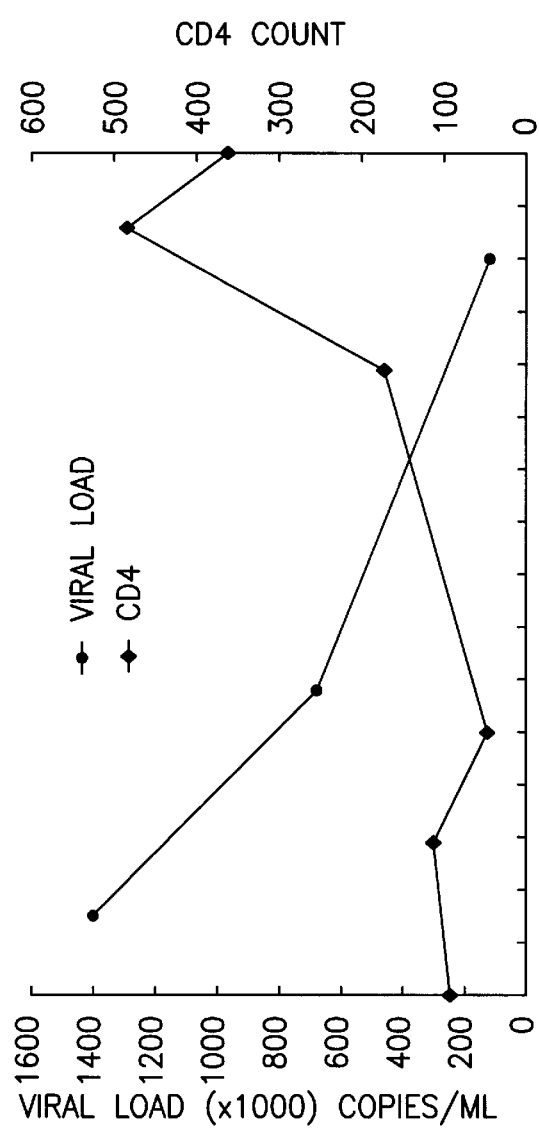

United States Patent [19]
Gallo et al.

[11] Patent Number: 5,997,871
[45] Date of Patent: Dec. 7, 1999

[54] TREATMENT AND PREVENTION OF CANCER BY ADMINISTRATION OF DERIVATIVES OF HUMAN CHORIONIC GONADOTROPIN

[75] Inventors: Robert C. Gallo, Bethesda; Joseph Bryant, Rockville; Yanto Lunardi-Iskandar, Gaithersburg, all of Md.

[73] Assignee: University of Maryland Biotechnology Insitute, College Park, Md.

[21] Appl. No.: 08/709,925

[22] Filed: Sep. 9, 1996

Related U.S. Application Data

[63] Continuation-in-part of application No. 08/669,676, Jun. 24, 1996, abandoned.

[51] Int. Cl.$^6$ .......................... A61K 39/00; A61K 38/03; A61K 38/24
[52] U.S. Cl. ................... 424/185.1; 424/198.1; 514/15
[58] Field of Search .............. 424/198.1, 185.1; 514/15

[56] References Cited

U.S. PATENT DOCUMENTS

| | | |
|---|---|---|
| 4,161,519 | 7/1979 | Talwar . |
| 4,400,316 | 8/1983 | Katsuragi et al. . |
| 4,689,222 | 8/1987 | McMichael . |
| 4,691,006 | 9/1987 | Stevens . |
| 4,692,332 | 9/1987 | McMichael . |
| 4,767,842 | 8/1988 | Stevens . |
| 4,780,312 | 10/1988 | Talwar . |
| 4,855,285 | 8/1989 | Stevens . |
| 4,880,626 | 11/1989 | McMichael . |
| 4,966,753 | 10/1990 | McMichael . |
| 5,380,668 | 1/1995 | Herron . |
| 5,451,527 | 9/1995 | Sarin et al. . |
| 5,700,781 | 12/1997 | Harris ................................ 514/21 |
| 5,811,390 | 9/1998 | Bourinbaiar ........................ 514/8 |
| 5,877,148 | 3/1999 | Lunardi-Iskandar et al. ........ 514/8 |

FOREIGN PATENT DOCUMENTS

| | | |
|---|---|---|
| 0 049 898 B2 | 4/1982 | European Pat. Off. . |
| 0 142 387 A1 | 5/1985 | European Pat. Off. . |
| WO 90/02759 | 3/1990 | WIPO . |
| WO 94/20859 | 9/1994 | WIPO . |
| WO 94/24148 | 10/1994 | WIPO . |
| WO 95/12299 | 5/1995 | WIPO . |
| WO 96/04008 | 2/1996 | WIPO . |

OTHER PUBLICATIONS

1996 Sigma Product Catalogue, p. 1134.
Bellet et al., 1984, Endocrinology 115:330–336.
Bidart et al., 1990, Science 248:736–739.
Bidart et al., 1987, J. Biol. Chem. 262:15483–15489.
Bidart et al., 1987, Mol. Immunology 24:339–345.
Braunstein et al., 1978, J. Clin. Endocrinology and Metabolism 47:326–332.
Caraux et al., 1985, J. Immunol. 134:835–840.
Chak et al., 1988, J. Clin. Oncol. 6:863–867.
De et al., 1997, J. Clin. Inv. 99:1484–1491.
Delli–Bovi et al., 1986, Cancer Res. 46:6333–6338.
Deshmukh et al., 1994, J. Clin. Immunol. 14:162:168.
Dirnhofer et al., 1994, J. Endocrinology 141:153–162.
Dirnhofer et al., 1993, FASEB J. 7:1381–1385.
Ensoli et al., 1989, Science 243:223–226.
Evans et al., 1991, J. Immunother. 10:39–50.
Friedman–Kien et al., 1981, J. Am. Acad. Dermatol. 5:468–473.
Gelmann et al., 1987, Am. J. Med. 82:456–462.
Gill et al., 1994, AIDS 8:1695–1699.
Gill et al., 1991, Am. J. Med. 90:427–433.
Gill et al., 1990, Am. J. Clin. Oncol. 13:315–319.
Gill et al., 1996, New Eng. J. Med. 335:1261–1269.
Harris, 1995, Lancet 346:118–119.
Hermans et al., 1995, AIDS Res. Hum. Retroviruses S:96.
Iyer et al., 1992, Int. J. Pepetide Protein Res. 39:137–144.
Keutmann et al., 1987, Proc. Natl. Acad. Sci. USA 84:2038–2042.
Keutmann et al., 1988, Biochemistry 27:8939–8944.
Kornyei et al., 1993, Biol. Reprod. 49:1149.
Krown et al., 1990, Ann. Intern. Med. 112:812–821.
Lapthorn et al., 1994, Nature 369:455–461.
Longhi et al., 1986, J. Immunol. Meth. 92:89–95.
Lunardi–Iskandar et al., 1995, Nature 375:64–68.
Lunardi–Iskandar et al., 1995, JNCI 87:974–981.
Masood et al., 1994, AIDS Res. Hum. Retroviruses 10:969–976.
Nakamura et al., 1988, Science 242:426–430.
Popescu et al., 1995, JNCI 88:450–454.
Puisieux et al., 1990, Endocrinology 126:687–694.
Ryan et al., 1988, FASEB J. 2:2661–2669.
Salahuddin et al., 1988, Science 242:430–433.
Siegal et al., 1990, Cancer 65:492–498.
Stevens et al., 1986, Immunol. Lett. 12:11–18.
Torres et al., 1987, Immunol. Inv. 16:607–618.
Triozzi et al., 1994, Int. J. Oncol. 5:1447–1453.
Vaslin et al., 1994, AIDS Res. Hum. Retroviruses 10:1241–1250.
Ward et al., 1991, *Reproduction in Domestic Animals* (Academic Press, New York) pp.25–80.
Weinroth et al., 1995, Infectious Agents and Disease 4:76–94.
Xia, 1993, J. Mol. Endocrinol. 337–343.
Yunis, 1983, Science 221:227–236.

*Primary Examiner*—Paula K. Hutzell
*Assistant Examiner*—Geetha P. Bansal
*Attorney, Agent, or Firm*—William A. Barrett; Steven J. Hultquist

[57] ABSTRACT

The present invention relates to methods of treating or preventing cancer by administration of human chorionic gonadotropin, β-human chorionic gonadotropin or a peptide containing a sequence of a portion of β-human chorionic gonadotropin. In a preferred embodiment, the invention provides methods of treating or preventing Kaposi's Sarcoma, breast cancer or prostate cancer. in another preferred embodiment, the invention relates to β-human chorionic gonadotropin peptides for treatment or prevention of cancer. The invention further provides assays for the utility of particular human chorionic gonadotropin preparations in the treatment or prevention of cancer. Pharmaceutical compositions and methods of administration are also provided.

38 Claims, 10 Drawing Sheets

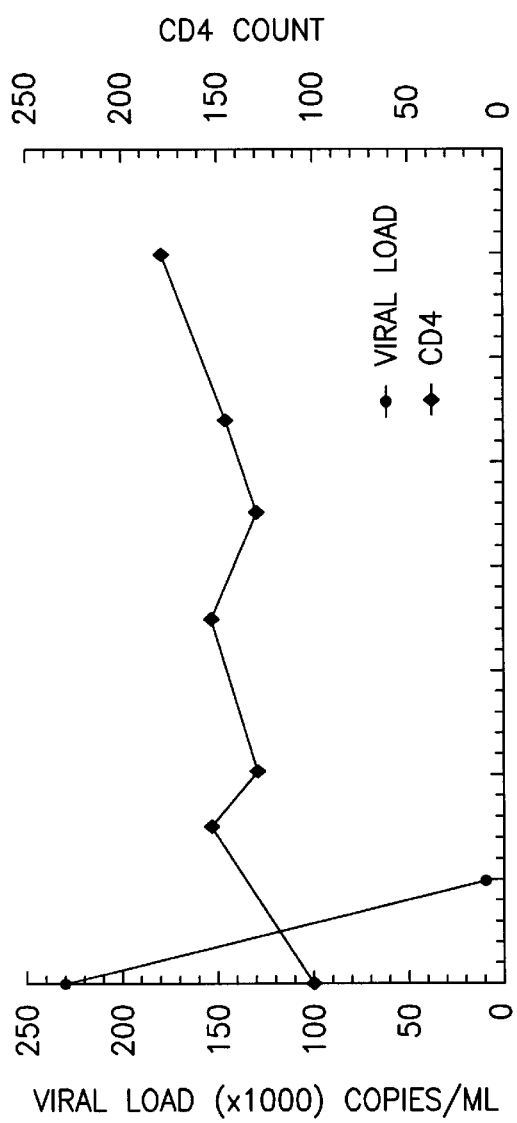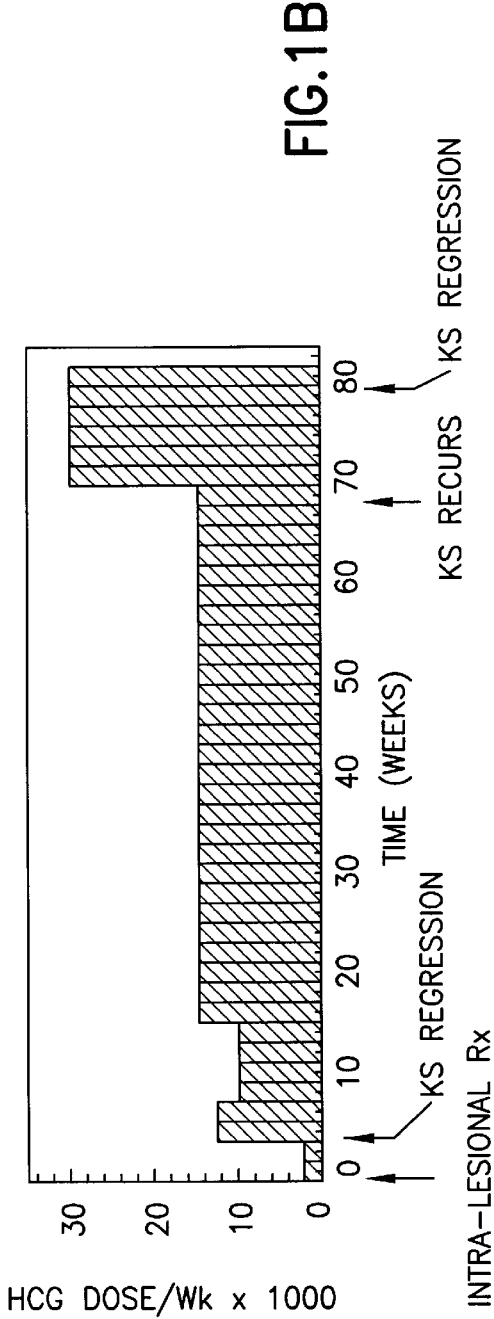

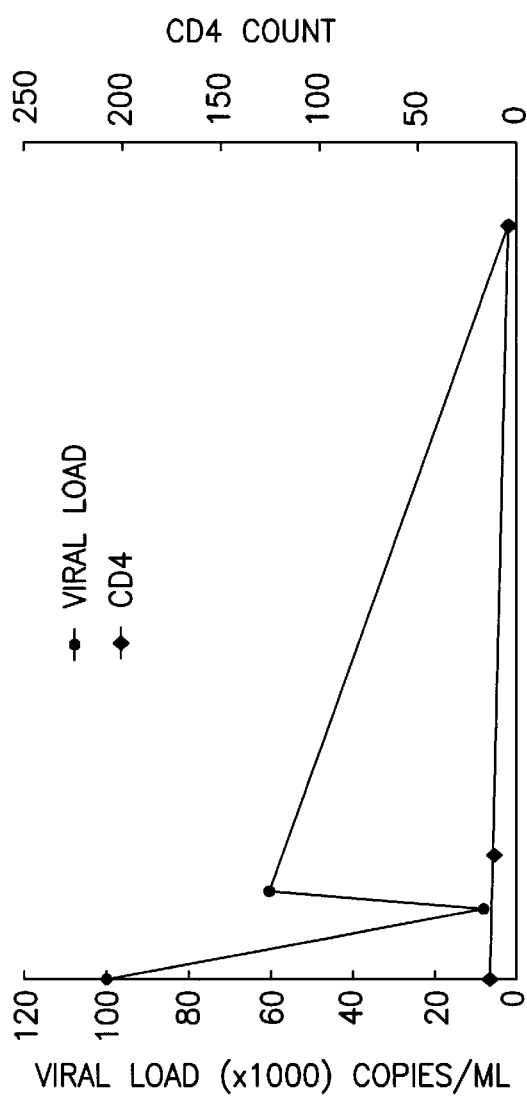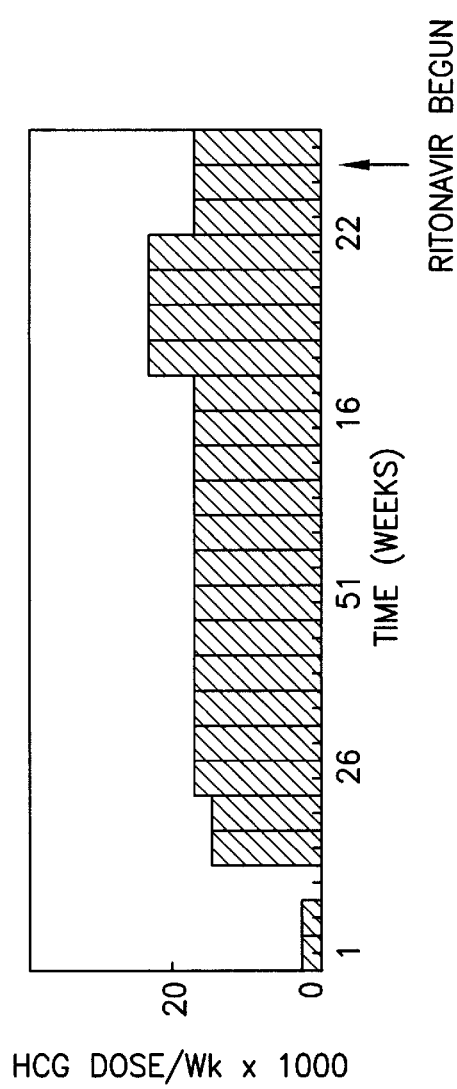

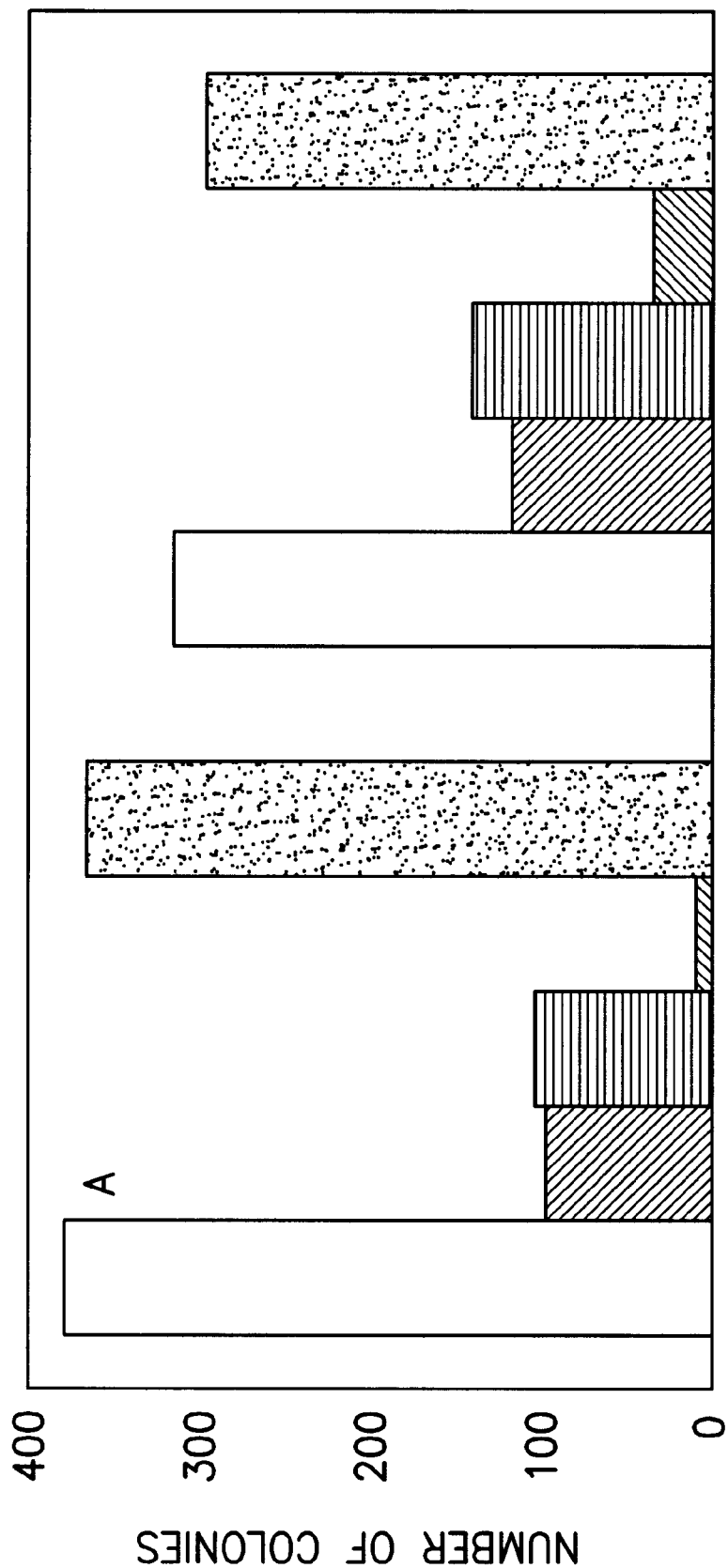

| FIG.3A |
|---|
| FIG.3B |
| FIG.3C |

FIG.3

FIG.3A

AGACAAGGCA GGGGACGCAC CAAGG ATG GAG ATG TTC CAG GGG CTG CTG CTG    52
                                Met Glu Met Phe Gln Gly Leu Leu Leu
                                                        -15

TTG CTG CTG CTG AGC ATG GGC GGG ACA TGG GCA TCC AAG GAG CCG CTT   100
Leu Leu Leu Leu Ser Met Gly Gly Thr Trp Ala Ser Lys Glu Pro Leu
-10                      -5                       1            5

CGG CCA CGG TGC CGC CCC ATC AAT GCC ACC CTG GCT GTG GAG AAG GAG   148
Arg Pro Arg Cys Arg Pro Ile Asn Ala Thr Leu Ala Val Glu Lys Glu
        10                       15                      20

```
GGC TGC CCC GTG TGC ATC ACC AAC ACC ATC TGT GCC GGC TAC            196
Gly Cys Pro Val Cys Ile Thr Asn Thr Ile Cys Ala Gly Tyr
                25                  30                  35

TGC CCC ACC ATG ACC CGC GTG CTG CAG GGG GTC CTG CCG GCC CTG CCT    244
Cys Pro Thr Met Thr Arg Val Leu Gln Gly Val Leu Pro Ala Leu Pro
        40                  45                  50

CAG GTG GTG TGC AAC TAC CGC GAT GTG CGC TTC GAG TCC ATC CGG CTC    292
Gln Val Val Cys Asn Tyr Arg Asp Val Arg Phe Glu Ser Ile Arg Leu
        55                  60                  65

CCT GGC TGC CCG CGC GGC GTG AAC CCC GTG GTC TCC TAC GCC GTG GCT    340
Pro Gly Cys Pro Arg Gly Val Asn Pro Val Val Ser Tyr Ala Val Ala
        70                  75                  80              85

CTC AGC TGT CAA TGT GCA CTC TGC CGC CGC AGC ACC ACT GAC TGC GGG    388
Leu Ser Cys Gln Cys Ala Leu Cys Arg Arg Ser Thr Thr Asp Cys Gly
                90                  95                 100

GGT CCC AAG GAC CAC CCC TTG ACC TGT GAT GAC CCC CGC TTC CAG GAC    436
Gly Pro Lys Asp His Pro Leu Thr Cys Asp Asp Pro Arg Phe Gln Asp
        105                 110                 115
```

FIG. 3B

```
TCC TCT TCC TCA AAG GCC CCT CCC CCC AGC CTT CCA AGC CCA TCC CGA      484
Ser Ser Ser Lys Ala Pro Pro Pro Pro Ser Leu Pro Ser Pro Ser Arg
            120                     125                     130

CTC CCG GGG CCC TCG GAC ACC CCG ATC CTC CCA CAA TAAAGGCTTC           530
Leu Pro Gly Pro Ser Asp Thr Pro Ile Leu Pro Gln
        135                     140                 145

TCAATCCGC                                                            539
```

FIG. 3C

5,997,871

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
        (A) LENGTH: 539 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 26..520

(xi) SEQUENCE DESCRIPTION: SEQ ID NO:1:

```
AGACAAGGCA GGGGACGCAC CAAGG ATG GAG ATG TTC CAG GGG CTG CTG CTG         52
                              Met Glu Met Phe Gln Gly Leu Leu Leu
                              -20                 -15

TTG CTG CTG CTG AGC ATG GGC GGG ACA TGG GCA TCC AAG GAG CCG CTT        100
Leu Leu Leu Leu Ser Met Gly Gly Thr Trp Ala Ser Lys Glu Pro Leu
    -10                 -5                   1

CGG CCA CGG TGC CGC CCC ATC AAT GCC ACC CTG GCT GTG GAG AAG GAG        148
Arg Pro Arg Cys Arg Pro Ile Asn Ala Thr Leu Ala Val Glu Lys Glu
                10                  15                  20

GGC TGC CCC GTG TGC ATC ACC GTC AAC ACC ACC ATC TGT GCC GGC TAC        196
Gly Cys Pro Val Cys Ile Thr Val Asn Thr Thr Ile Cys Ala Gly Tyr
            25                  30                  35

TGC CCC ACC ATG ACC CGC GTG CTG CAG GGG GTC CTG CCG GCC CTG CCT        244
Cys Pro Thr Met Thr Arg Val Leu Gln Gly Val Leu Pro Ala Leu Pro
            40                  45                  50

CAG GTG GTG TGC AAC TAC CGC GAT GTG CGC TTC GAG TCC ATC CGG CTC        292
Gln Val Val Cys Asn Tyr Arg Asp Val Arg Phe Glu Ser Ile Arg Leu
    55                  60                  65

CCT GGC TGC CCG CGC GGC CTG AAC CCC GTG GTC TCC TAC GCC GTG GCT        340
Pro Gly Cys Pro Arg Gly Leu Asn Pro Val Val Ser Tyr Ala Val Ala
70                  75                  80                  85

CTC AGC TGT CAA TGT GCA CTC TGC CGC CGC AGC ACC ACT GAC TGC GGG        388
Leu Ser Cys Gln Cys Ala Leu Cys Arg Arg Ser Thr Thr Asp Cys Gly
                90                  95                 100

GGT CCC AAG GAC CAC CCC TTG ACC TGT GAT GAC CCC CGC TTC CAG GAC        436
Gly Pro Lys Asp His Pro Leu Thr Cys Asp Asp Pro Arg Phe Gln Asp
            105                 110                 115

TCC TCT TCC TCA AAG GCC CCT CCC CCC AGC CTT CCA AGC CCA TCC CGA        484
Ser Ser Ser Ser Lys Ala Pro Pro Pro Ser Leu Pro Ser Pro Ser Arg
            120                 125                 130

CTC CCG GGG CCC TCG GAC ACC CCG ATC CTC CCA CAA TAAAGGCTTC             530
Leu Pro Gly Pro Ser Asp Thr Pro Ile Leu Pro Gln
            135                 140                 145
```

TCAATCCGC                                                              539

(2) INFORMATION FOR SEQ ID NO:2:

(i) SEQUENCE CHARACTERISTICS:
        (A) LENGTH: 165 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Met Phe Gln Gly Leu Leu Leu Leu Leu Leu Ser Met Gly
-20              -15             -10              -5

Gly Thr Trp Ala Ser Lys Glu Pro Leu Arg Pro Arg Cys Arg Pro Ile
                 1               5                   10

Asn Ala Thr Leu Ala Val Glu Lys Glu Gly Cys Pro Val Cys Ile Thr
            15              20              25

Val Asn Thr Thr Ile Cys Ala Gly Tyr Cys Pro Thr Met Thr Arg Val
        30              35              40

Leu Gln Gly Val Leu Pro Ala Leu Pro Gln Val Val Cys Asn Tyr Arg
    45              50              55              60

Asp Val Arg Phe Glu Ser Ile Arg Leu Pro Gly Cys Pro Arg Gly Leu
                65              70              75

Asn Pro Val Val Ser Tyr Ala Val Ala Leu Ser Cys Gln Cys Ala Leu
            80              85              90

Cys Arg Arg Ser Thr Thr Asp Cys Gly Gly Pro Lys Asp His Pro Leu
                95              100             105

Thr Cys Asp Asp Pro Arg Phe Gln Asp Ser Ser Ser Lys Ala Pro
    110             115             120

Pro Pro Ser Leu Pro Ser Pro Ser Arg Leu Pro Gly Pro Ser Asp Thr
125             130             135             140

Pro Ile Leu Pro Gln
                145

(2) INFORMATION FOR SEQ ID NO:3:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:3:

Met Thr Arg Val Leu Gln Gly Val Leu Pro Ala Leu Pro Gln
1               5                   10

(2) INFORMATION FOR SEQ ID NO:4:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:4:

Leu Gln Gly Val Leu Pro Ala Leu Pro Gln
1               5                   10

(2) INFORMATION FOR SEQ ID NO:5:

```
       (i) SEQUENCE CHARACTERISTICS:
           (A) LENGTH: 7 amino acids
           (B) TYPE: amino acid
           (D) TOPOLOGY: linear (ii) MOLECULE TYPE: peptide (xi) SEQUENCE DESCRIPTION: SEQ ID NO:5:

Gly Val Leu Pro Ala Leu Pro
1               5

(2) INFORMATION FOR SEQ ID NO:6:

(i) SEQUENCE CHARACTERISTICS:
           (A) LENGTH: 13 amino acids
           (B) TYPE: amino acid
           (D) TOPOLOGY: linear (ii) MOLECULE TYPE: peptide (xi) SEQUENCE DESCRIPTION: SEQ ID NO:6:

Leu Gln Gly Val Leu Pro Ala Leu Pro Gln Val Val Cys
1               5                   10

(2) INFORMATION FOR SEQ ID NO:7:

(i) SEQUENCE CHARACTERISTICS:
           (A) LENGTH: 11 amino acids
           (B) TYPE: amino acid
           (D) TOPOLOGY: both (ii) MOLECULE TYPE: peptide (xi) SEQUENCE DESCRIPTION: SEQ ID NO:7:

Thr Cys Asp Asp Pro Arg Phe Gln Asp Ser Ser
1               5                   10

(2) INFORMATION FOR SEQ ID NO:8:

(i) SEQUENCE CHARACTERISTICS:
           (A) LENGTH: 13 amino acids
           (B) TYPE: amino acid
           (D) TOPOLOGY: linear (ii) MOLECULE TYPE: peptide (xi) SEQUENCE DESCRIPTION: SEQ ID NO:8:

Met Thr Arg Val Leu Gln Gly Val Leu Pro Ala Leu Pro
1               5                   10

(2) INFORMATION FOR SEQ ID NO:9:

(i) SEQUENCE CHARACTERISTICS:
           (A) LENGTH: 12 amino acids
           (B) TYPE: amino acid
           (D) TOPOLOGY: linear (ii) MOLECULE TYPE: peptide (xi) SEQUENCE DESCRIPTION: SEQ ID NO:9:

Thr Arg Val Leu Gln Gly Val Leu Pro Ala Leu Pro
1               5                   10

(2) INFORMATION FOR SEQ ID NO:10:

(i) SEQUENCE CHARACTERISTICS:
           (A) LENGTH: 11 amino acids
           (B) TYPE: amino acid
           (D) TOPOLOGY: linear
```

(ii) MOLECULE TYPE: peptide (xi) SEQUENCE DESCRIPTION: SEQ ID NO:10:

Arg Val Leu Gln Gly Val Leu Pro Ala Leu Pro
1               5                   10

(2) INFORMATION FOR SEQ ID NO:11:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:11:

Val Leu Gln Gly Val Leu Pro Ala Leu Pro
1               5                   10

(2) INFORMATION FOR SEQ ID NO:12:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (xi) SEQUENCE DESCRIPTION: SEQ ID NO:12:

Val Leu Gln Gly Val Leu Pro Ala Leu Pro Gln Val Val Cys
1               5                   10

(2) INFORMATION FOR SEQ ID NO:13:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (xi) SEQUENCE DESCRIPTION: SEQ ID NO:13:

Leu Gln Gly Val Leu Pro Ala Leu Pro
1               5

(2) INFORMATION FOR SEQ ID NO:14:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:14:

Gln Gly Val Leu Pro Ala Leu Pro
1               5

(2) INFORMATION FOR SEQ ID NO:15:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:15:

Leu Gln Gly Val Leu Pro Ala Leu Pro Gln

```
1               5                  10
```

(2) INFORMATION FOR SEQ ID NO:16:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:16:

```
Leu Gln Gly Val Leu Pro Ala Leu Pro Gln Val
1               5                  10
```

(2) INFORMATION FOR SEQ ID NO:17:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:17:

```
Leu Gln Gly Val Leu Pro Ala Leu Pro Gln Val Val
1               5                  10
```

(2) INFORMATION FOR SEQ ID NO:18:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:18:

```
Leu Gln Gly Val Leu Pro Ala Leu Pro Gln Val Val Cys Asn
1               5                  10
```

(2) INFORMATION FOR SEQ ID NO:19:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:19:

```
Gly Val Leu Pro Ala Leu Pro Gln
1               5
```

(2) INFORMATION FOR SEQ ID NO:20:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:20:

```
Gly Val Leu Pro Ala Leu Pro Gln Val
1               5
```

(2) INFORMATION FOR SEQ ID NO:21:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:21:

Gly Val Leu Pro Ala Leu Pro Gln Val Val
1               5                   10

(2) INFORMATION FOR SEQ ID NO:22:

(i) SEQUENCE CHARACTERISTICS:
            (A) LENGTH: 12 amino acids
            (B) TYPE: amino acid
            (D) TOPOLOGY: linear (ii) MOLECULE TYPE: peptide (xi) SEQUENCE DESCRIPTION: SEQ ID NO:22:

Gly Val Leu Pro Ala Leu Pro Gln Val Val Cys Asn
1               5                   10

(2) INFORMATION FOR SEQ ID NO:23:

(i) SEQUENCE CHARACTERISTICS:
            (A) LENGTH: 98 amino acids
            (B) TYPE: amino acid
            (D) TOPOLOGY: linear (ii) MOLECULE TYPE: peptide (xi) SEQUENCE DESCRIPTION: SEQ ID NO:23:

Val Leu Pro Ala Leu Pro Gln Val Val Cys Asn Tyr Arg Asp Val Arg
1               5                   10                  15

Phe Glu Ser Ile Arg Leu Pro Gly Cys Pro Arg Gly Leu Asn Pro Val
                20                  25                  30

Val Ser Tyr Ala Val Ala Leu Ser Cys Gln Cys Ala Leu Cys Arg Arg
            35                  40                  45

Ser Thr Thr Asp Cys Gly Gly Pro Lys Asp His Pro Leu Thr Cys Asp
        50                  55                  60

Asp Pro Arg Phe Gln Asp Ser Ser Ser Lys Ala Pro Pro Ser
65                  70                  75                  80

Leu Pro Ser Pro Ser Arg Leu Pro Gly Pro Ser Asp Thr Pro Ile Leu
                85                  90                  95

Pro Gln (2) INFORMATION FOR SEQ ID NO:24:

(i) SEQUENCE CHARACTERISTICS:
            (A) LENGTH: 88 amino acids
            (B) TYPE: amino acid
            (D) TOPOLOGY: linear (ii) MOLECULE TYPE: peptide (xi) SEQUENCE DESCRIPTION: SEQ ID NO:24:

Asn Tyr Arg Asp Val Arg Phe Glu Ser Ile Arg Leu Pro Gly Cys Pro
1               5                   10                  15

Arg Gly Leu Asn Pro Val Val Ser Tyr Ala Val Ala Leu Ser Cys Gln
                20                  25                  30

Cys Ala Leu Cys Arg Arg Ser Thr Thr Asp Cys Gly Gly Pro Lys Asp
            35                  40                  45

```
His Pro Leu Thr Cys Asp Asp Pro Arg Phe Gln Asp Ser Ser Ser Ser
    50              55              60

Lys Ala Pro Pro Pro Ser Leu Pro Ser Pro Ser Arg Leu Pro Gly Pro
65              70              75              80

Ser Asp Thr Pro Ile Leu Pro Gln
                85

(2) INFORMATION FOR SEQ ID NO:25:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (xi) SEQUENCE DESCRIPTION: SEQ ID NO:25:

Thr Cys Asp Asp Pro Arg Phe Gln Asp Ser Ser Ser Lys Ala Pro
1               5               10              15

Pro Pro Ser Leu Pro Ser Pro Ser Arg Leu Pro Gly Pro Ser Asp Thr
            20              25              30

Pro Ile Leu Pro Gln
        35

(2) INFORMATION FOR SEQ ID NO:26:

(i) SEQUENCE CHARACTERISTICS:
        (A) LENGTH: 14 amino acids
        (B) TYPE: amino acid
        (D) TOPOLOGY: circular (ii) MOLECULE TYPE: peptide (xi) SEQUENCE DESCRIPTION: SEQ ID NO:26:

Cys Leu Gln Gly Val Leu Pro Ala Leu Pro Gln Val Val Cys
1               5               10
```

TREATMENT AND PREVENTION OF CANCER BY ADMINISTRATION OF DERIVATIVES OF HUMAN CHORIONIC GONADOTROPIN

1. CROSS REFERENCE TO RELATED APPLICATION

This application is a continuation in part of application Ser. No. 08/669,676, filed Jun. 24, 1996 (now abandoned), which is incorporated by reference herein in its entirety.

2. FIELD OF THE INVENTION

The present invention is directed to methods of treatment and prevention of cancer by administration of human chorionic gonadotropin, the β-chain of human chorionic gonadotropin and peptides containing a sequence of a portion of the β-chain of human chorionic gonadotropin. The invention also provides pharmaceutical compositions comprising human chorionic gonadotropin, the β-chain of human chorionic gonadotropin or peptides having a sequence of a portion of the β-chain of human chorionic gonadotropin.

3. BACKGROUND OF THE INVENTION

3.1. Cancer

A neoplasm, or tumor, is a neoplastic mass resulting from abnormal uncontrolled cell growth, which may cause swelling on the body surface, and which can be benign or malignant. Benign tumors generally remain localized. Malignant tumors are collectively termed cancers. The term "malignant" generally means that the tumor can invade and destroy neighboring body structures and spread to distant sites to cause death (for review, see Robbins and Angell, 1976, *Basic Pathology*, 2d Ed., W.B. Saunders Co., Philadelphia, pp. 68–122). Treatment options, such as surgery, chemotherapy and radiation treatment, are either ineffective or present serious side effects. Thus, there is a need for development of new drugs for the treatment of cancer.

Kaposi's Sarcoma (KS) is a rare type of cancer, the incidence of which is greatly increased in HIV infected people (Lunardi-Iskandar, Y., et al., 1995, *Nature* 375:64–68; Friedman-Kien, A. E., et al., 1981, *J. Am. Acad. Dermatol.* 5:468–473). The tumors appear to be comprised of hyperplastic cells derived from vascular endothelial cells (Nakamura, S., et al., 1988, *Science* 242:426–430; Ensoli, B., et al, 1989, *Science* 243:223–226; Salahuddin, S. Z., et al., 1988, *Science* 242:430–433; Masood, R., et al., 1994, *AIDS Res. Hum. Retroviruses* 10:969–976; Lunardi-Iskandar, Y., et al., 1995, *JNCI* 88:450–454). In some cases, neoplastic cells with chromosomal abnormalities are also present in the tumors (Lunardi-Iskandar, Y., et al., 1995, *JNCI* 87:974–981; Delli-Bovi, P., et al., 1986, *Cancer Res.* 46:6333–6338; Siegal, B., et al., 1990, *Cancer* 65:492–498; Yunis, J. J., 1983, *Science* 221:227–236; Popescu, N. C., et al., 1995, *JNCI* 88:450–454). Therapies for KS include radiotherapy, α-interferon and systemic chemotherapy (Chak, L. Y., et al., 1988, *J. Clin. Oncol.* 6:863–7; Evans, L. M., et al., 1991, *J. Immunother.* 10:39–50; Kovas, J., et al., 1990, *Ann. Intern. Med.* 112:812–21; Gelmann, E. D., et al., 1987, *Am. J. Med.* 82:456–62; Gill, P. S., et al., 1991, *Am. J. Med.* 90:427–33; Gill, P. S., et al., 1990; *Am. J. Clin. Oncol.* 13:315–9; Gill, P. S., et al., 1994, *AIDS* 8:1695–9). However, hematological and non-hematological toxicities limit the prolonged use of chemotherapy and α-interferon in conjunction with anti-retroviral agents commonly used in the treatment of AIDS (Kovas, J., et al., 1990, *Ann. Intern. Med.* 112:812–21; Gill, P. S., et al., 1991, *Am. J. Med.* 90:427–33; Gill, P. S., et al., 1994, *AIDS* 8:1695–9). Thus, new drugs, preferably drugs compatible with AIDS therapeutics, are needed for the treatment of KS.

3.2. Human Chorionic Gonadotropin

Human chorionic gonadotropin (hCG), which is required for the maintenance of pregnancy, is a member of the glycoprotein hormone family. The glycoprotein hormones, which also include follicle-stimulating hormone (FSH), luteinizing hormone (LH) and thyroid-stimulating hormone (TSH), consist of two sub-units, α and β. These subunits are non-covalently linked to form a heterodimer, and heterodimer formation has been shown to be required for receptor binding. Within a particular species, the α-subunits are identical among the glycoprotein hormones while the β-subunits differ and determine the receptor binding specificity of the particular hormone (Kornyei, J. L., et al., 1993, *Biol. Reprod.* 49:1149). The β-subunits of the glycoprotein hormones exhibit a high degree of sequence similarity within the N-terminal 114 amino acids. LH is the most similar to hCG with 85% sequence homology within the first 114 amino acids, and both proteins bind the same receptor. hCG, however, contains a C-terminal extension not present in the other glycoprotein β-chains (Lapthorn, A. J., et al., 1994, *Science* 369:455–461).

From the three dimensional crystal structure of hCG, it was determined that hCG, like the growth factors nerve growth factor (NGF), transforming growth factor-β (TGF-β) and platelet-derived growth factor-β (PDGF-β), is a cysteine-knot glycoprotein. Proteins containing such a cysteine-knot motif have at least three disulfide bridges, two of which join adjacent anti-parallel strands of the peptide, thus, forming a ring, and one of which joins the peptide chain through the ring. Particular structures in the hCG β-chain include the determinant loop sequence (β93-100) which has been implicated in subunit association and the longest inter-cysteine loop (β38-57) which may play a role in receptor binding. Residues 47-53 appear to be exposed at the surface of this inter-cysteine loop (Lapthorn et al., 1994, *Nature* 369:455–461).

References by Bellet et al. (PCT Publication WO94/20859; Australian Patent Publication AU 94/62112; PCT Publication WO95/12299) disclose the use of hCG or certain peptides thereof for immunotherapy treatment of cancers which secrete hCG or hCG fragments. None of these references, however, describe the administration of the β-hCG peptides of the present invention.

Triozzi et al. (1994, *Int. J. Oncology* 5:1447–1453) describes the use of a synthetic β-hCG vaccine for treatment of a variety of non-trophoblastic cancers by production of an immune response against a portion of hCG. The only vaccine disclosed in the reference consists of the carboxy terminal peptide of β-hCG (amino acids 109–145) conjugated to diphtheria toxoid. Furthermore, Stevens (U.S. Pat. No. 4,691,006) used modified peptides for treatment of, inter alia, hormone-related diseases and disorders and hormone-associated carcinomas. C-terminal β-hCG peptides, i.e., peptides and subpeptides of amino acids 111–145, which have been modified in some way are described for use in treating hCG secreting cancers. The patent specifically indicates that peptides from amino acids 1–110 of β-hCG are not useful for treating such cancers.

Lunardi-Iskandar et al. (1995, *Nature* 375:64–68 and PCT Publication WO96/04008) discloses that hCG, β-hCG, as well as β-hCG carboxy-terminal peptides of amino acids 109–145 (SEQ ID NO:25) and 109–119 (SEQ ID NO:7) are useful for treatment of Kaposi's Sarcoma. Phase II clinical trials have been carried out in which intralesional injections with some commercial preparations of hCG resulted in remissions of KS lesions (Gill, P. S., et al., 1996, *New Eng. J. Med.*, submitted) and systemic injection resulted in regression of far advanced pulmonary KS in two patients (Hermans, P., et al., 1995, *AIDS Res. Hum. Retroviruses* S:96). Harris (1995, *The Lancet* 346:118–119) reported that high doses of hCG, specifically 150,000 IU to 700,000 IU three times per week intramuscularly, but not doses of 100,000 IU three times per week given intramuscularly lead to KS tumor regression in certain KS patients. However, none of these references suggests using the peptides of the present invention.

Citation of references hereinabove shall not be construed as an admission that such references are prior art to the present invention.

4. SUMMARY OF THE INVENTION

The present invention relates to therapeutic methods and compositions for treatment and prevention of cancers based on hCG, β-hCG and therapeutically and prophylactically effective peptides containing a sequence of a portion of β-hCG. The invention provides for treatment and prevention of cancer by administration of a therapeutic compound of the invention. The therapeutic compounds of the invention include: hCG, β-hCG, therapeutically effective peptides containing a sequence of a portion of β-hCG, analogs and derivatives of hCG, β-hCG and peptides having a sequence of a portion of β-hCG, and nucleic acids encoding hCG, β-hCG and peptides having a sequence of a portion of β-hCG, and derivatives and analogs thereof. In a preferred embodiment, the therapeutic comprises a β-hCG peptide, the amino acid sequence of which consists of amino acid numbers 41–54 (SEQ ID NO:3), 45–54 (SEQ ID NO:4), 47–53 (SEQ ID NO:5) or 45–57 (SEQ ID NO:6) of the β-hCG sequence depicted in FIG. 3 (a portion of SEQ ID NO:2).

The invention further provides assays, both in vitro and in vivo, for testing the efficacy of the Therapeutics of the invention.

The invention also provides methods of administration and pharmaceutical compositions containing a Therapeutic of the invention.

5. DESCRIPTION OF THE FIGURES

FIGS. 1A–F. Effects of some hCG preparations on HIV-1 viral load, CD4$^+$ T cell levels, and weight over extended periods in individual patients with advanced HIV infection. (A and B) Bar graphs depicting the results from hCG treatment of patient PH-VE (see Table 2) over time in weeks. (A) Graph presents data of CD4$^+$ T cell count in mm$^3$ (line with diamonds) and viral load as copies×1000/ml plasma (line with circles). (B) Graph documents the status of the patient's Kaposi's sarcoma with respect to the dosages of hCG administered, indicated as IU×1000/week. At week 0, intralesional therapy began; at week 3, regression of KS lesions was observed; at week 68, KS lesions recurred; and at week 79, KS lesion regression was observed. (C and D) Bar graphs depicting the results of hCG treatment of patient PH-SPBE (see Table 2) over time in weeks. (C) Graph presents data of CD4$^+$ T cell count in mm$^3$ (line with diamonds) and viral load as copies (×1000)/ml plasma (line with circles). (D) Bar graph indicates the dosage of hCG per week in IU×1000. It is noted beneath the graph that ritonavir therapy was begun at 20 weeks of therapy. (E and F) Bar graphs depicting the results from hCG treatment of patient PH-VE (see Table 2) over time in weeks. (E) Graph presents data of CD4$^+$ T cell count in mm$^3$ (line with diamonds) and viral load as copies (×1000)/mL plasma (line with circles). (F) Bar graph indicates the dosage of hCG per week in IU×1000. It is noted beneath the graph that ritonavir therapy was begun after 20 weeks of therapy.

FIGS. 2A–H. Effect of hCG preparations and peptides on KS colony growth in vitro and KS tumors in vivo. (A) Comparison of the anti-KS in vitro effects (tumor cell killing) of purified hCG and β-hCG peptides in KS clonogenic assays using KS Y-12 and KS "SKL"18 cells depicted in a bar graph in terms of number of colonies. The results are averages of 3 sets of results with less than 10% variation and are representative of multiple experiments. Results with no hCG or hCG peptides are represented by open bars, the results with the β-hCG peptide of amino acids 109–119 (SEQ ID NO:7) are represented by stippled bars, the results with the β-hCG peptide of amino acids 109–145 (SEQ ID NO:25) are represented by the bars with horizontal stripes, the results with the circular β-hCG peptide of amino acids 44–57 (SEQ ID NO:12) where the amino acid at position 44 is a cysteine are represented by the bars with diagonal stripes, and the results with the highly purified hCG preparation, CR 127, are represented by solid bars. (B–H) Thin sections of KS tumors induced in nude mice by inoculation with 10$^6$ neoplastic KS Y-1 cells. (B) Thin section of tumors from mice that were not treated with hCG or hCG subunits or peptides (C) Thin section of a tumor from a mouse after treatment with crude hCG APL (100 IU) subcutaneously daily for 7 days. (D) Thin section of a tumor from a mouse treated with the β-hCG peptide of amino acids 45-57 (SEQ ID NO:6), 10 μg/ml/daily (6.7 nmoles) for 5 days. (E) Thin section of a tumor from a mouse after 5 days of treatment with the circularized β-hCG peptide 44-57 (SEQ ID NO:12), where cysteine has been substituted at position 44, at 10 μg per day. (F) This panel shows the thin tissue section of KS tumor from AIDS-KS patients treated with 1 ml of diluent alone shows less than 2% cell death as detected by specific apoptosis in situ immunostaining. (G) Thin tissue section of KS tumor from an AIDS-KS patient after hCG preparation therapy of intralesional injections of 2000 IU, 3 times weekly for 2–3 weeks, shows evidence of apoptosis in all cells. (H) Thin tissue section of KS tumor from an AIDS-KS patient after hCG preparation therapy, 500 IU, 3 times weekly for 3 weeks.

FIG. 3. The nucleotide (SEQ ID NO:1) and amino acid (SEQ ID NO:2) sequences of β-hCG.

Figure 4A:
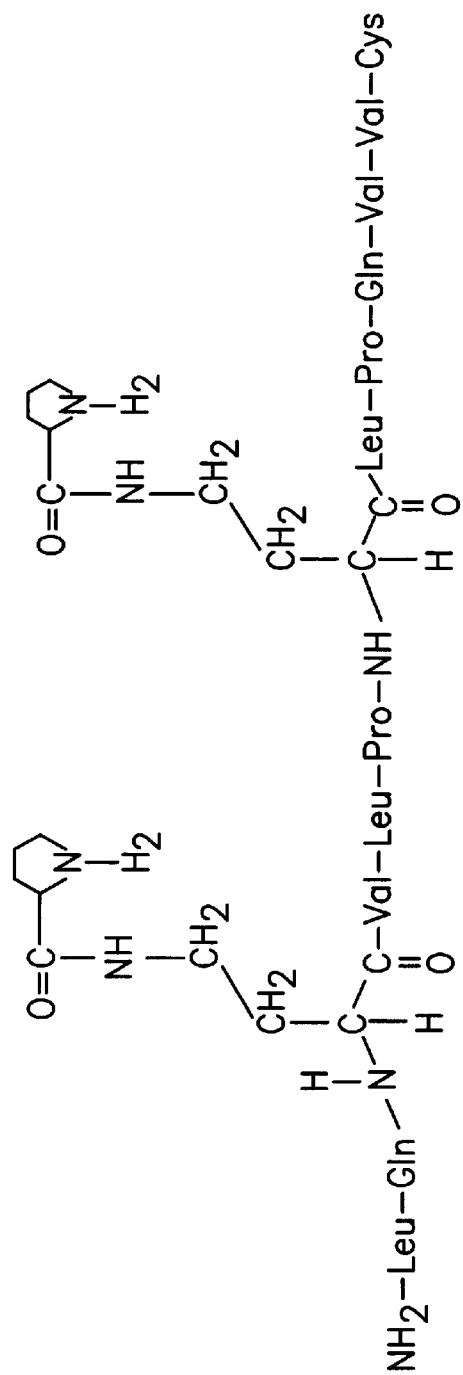

FIGS. 4A and B. Schematic depiction of the structures of (A) the linear peptide of amino acids 45-57 (SEQ ID NO:6) of the β-hCG sequence depicted in FIG. 8 (SEQ ID NO:2) where the amino acid residues at positions 47 and 51 are substituted by a branch made up of diaminobutyric acid peptide bonded to proline, and (B) the circularized peptide of amino acids 44-57 (SEQ ID NO:12) with valine at position 44 substituted with cysteine, which protein is circularized via a disulfide bond between its amino- and carboxy-terminal cysteines. In both A and B, amino acids are represented by their three letter amino acid code, except for the branched residues and the terminal cysteines, for which the structure is depicted.

6. DETAILED DESCRIPTION OF THE INVENTION

The present invention relates to therapeutic methods and compositions for treatment and prevention of cancer based on hCG, β-hCG and therapeutically or prophylactically effective proteins (e.g., peptides) having a sequence of a portion of β-hCG (β-hCG peptides). The invention provides for treatment and prevention of cancer by administration of a therapeutic compound of the invention. The therapeutic compounds of the invention include: hCG, β-hCG, therapeutically or prophylactically effective β-hCG peptides, analogs and derivatives of hCG, β-hCG or β-hCG peptides and nucleic acids encoding β-hCG and β-hCG peptides, and derivatives and analogs thereof. In a preferred embodiment, the therapeutic compound includes β-hCG peptides, particularly β-hCG peptides of amino acid numbers 41-54, 45-54, 47-53 or 45-57 (SEQ ID NOS:3–6, respectively) as depicted in FIG. 3 (a portion of SEQ ID NO:2).

In a preferred embodiment, a therapeutic composition of the invention comprises a β-hCG peptide, the amino acid sequence of which consists of amino acid numbers 41-53, 42-53, 43-53, 44-53, 44-57, 45-53, 46-53, 45-54, 45-55, 45-56, 45-58, 47-54, 47-55, 47-56, 47-58, 48-145, 58-145 or 109-145 (SEQ ID NOS:8–25, respectively) of FIG. 3 (a portion of SEQ ID NO:2), particularly a β-hCG peptide which consists of amino acid numbers 41-54, 45-54 or 109-119 (SEQ ID NOS:3, 4, or 7, respectively), most preferably of a β-hCG peptide which consists of amino acids 47-53 (SEQ ID NO:5) or 45-57 (SEQ ID NO:6). In other preferred embodiments, the therapeutic comprises a β-hCG peptide, the amino acid sequence of which consists of circularized (via a disulfide bond between its amino- and carboxy-terminal cysteines) 44-57 (SEQ ID NO:26) with the valine at position 44 substituted with cysteine ((Val44Cys) 45-57 circularized) (depicted in FIG. 4B), 45-57 (SEQ ID NO:6) where the amino acid residues at positions 47 and 51 are substituted by a branch, where the branches are made up of diaminobutyric acid peptide bonded to a proline residue (depicted in FIG. 4A). The amino acid sequence of β-hCG is depicted in FIG. 3 (SEQ ID NO:2).

For clarity of disclosure, and not by way of limitation, the detailed description of the invention is divided into the subsections which follow.

6.1. Therapeutic Uses

The invention provides for treatment or prevention of cancer by administration of a therapeutic compound (termed herein "Therapeutic") of the invention. Such "Therapeutics" include but are not limited to: hCG, β-hCG and derivatives thereof, and therapeutically or prophylactically effective β-hCG peptides, i.e., those peptides which prevent or treat cancer (e.g., as demonstrated in in vitro and in vivo assays described infra) as well as modifications, derivatives and analogs thereof and nucleic acids encoding hCG, β-hCG and therapeutically and prophylactically effective β-hCG peptides and derivatives and analogs thereof. In a preferred embodiment, the Therapeutic of the invention is a β-hCG peptide having a sequence of amino acid numbers 41-54, 45-54, 47-53 or 45-57 (SEQ ID NOS:3–6, respectively) of FIG. 3 (a portion of SEQ ID NO:2). In other embodiments, the Therapeutic of the invention is a β-hCG peptide having a sequence of amino acid numbers 41-53, 42-53, 43-53, 44-53, 44-57, 45-53, 46-53, 45-54, 45-55, 45-56, 45-58, 47-54, 47-55, 47-56, 47-58, 48-145, 58-145, 109-119 or 109-145 (SEQ ID NOS:8–24, 7 and 25 respectively) of FIG. 3 (a portion of SEQ ID NO:2). Additionally, the present inventors have found that different preparations of hCG and β-hCG have variable effects on KS tumors and cells both in vitro and in vivo. Specifically, the inventors found that among the (non-recombinant) commercial preparations they investigated, hCG from Fujisawa was the most effective, hCG from APL (Wyeth-Ayerst) the next most effective, and pregnyl (organon) the next most effective. hCG preparations or fractions of hCG preparations can be screened for utility in cancer treatment or prevention by the methods described infra in Section 5.2 or any method known in the art.

6.1.1. Treatment of Malignancies

Malignancies and related disorders that can be treated or prevented by administration of a Therapeutic of the invention include, but are not limited to, those disorders listed in Table 1 (for a review of such disorders, see Fishman et al., 1985, *Medicine*, 2d Ed., J.B. Lippencott Co., Philadelphia):

TABLE 1

| MALIGNANCIES AND RELATED DISORDERS |
|---|
| Leukemia |
|     acute leukemia |
|         acute lymphocytic leukemia |
|         acute myelocytic leukemia |
|             myeloblastic |
|             promyelocytic |
|             myelomonocytic |
|             monocytic |
|             erythroleukemia |
|     chronic leukemia |
|         chronic myelocytic (granulocytic) leukemia |
|         chronic lymphocytic leukemia |
| Polycythemia vera |
| Lymphoma |
|     Hodgkin's disease |
|     non-Hodgkin's disease |
| Multiple myeloma |
| Waldenstrom's macroglobulinemia |
| Heavy chain disease |
| Solid tumors |
|     sarcomas and carcinomas |
|         fibrosarcoma |
|         myxosarcoma |
|         liposarcoma |
|         chondrosarcoma |
|         osteogenic sarcoma |
|         chordoma |
|         angiosarcoma |
|         endotheliosarcoma |
|         lymphangiosarcoma |
|         Kaposi's sarcoma |
|         lymphangioendotheliosarcoma |
|         synovioma |
|         mesothelioma |
|         Ewing's tumor |
|         leiomyosarcoma |
|         rhabdomyosarcoma |
|         colon carcinoma |
|         pancreatic cancer |
|         breast cancer |
|         ovarian cancer |
|         prostate cancer |
|         squamous cell carcinoma |
|         basal cell carcinoma |
|         adenocarcinoma |
|         sweat gland carcinoma |
|         sebaceous gland carcinoma |
|         papillary carcinoma |
|         papillary adenocarcinomas |
|         cystadenocarcinoma |
|         medullary carcinoma |
|         bronchogenic carcinoma |
|         renal cell carcinoma |
|         hepatoma |
|         bile duct carcinoma |
|         choriocarcinoma |
|         seminoma |
|         embryonal carcinoma |
|         Wilms' tumor |
|         cervical cancer |
|         uterine cancer |
|         testicular tumor |
|         lung carcinoma |

TABLE 1-continued

MALIGNANCIES AND RELATED DISORDERS
small cell lung carcinoma
bladder carcinoma
epithelial carcinoma
glioma
astrocytoma
medulloblastoma
craniopharyngioma
ependymoma
pinealoma
hemangioblastoma
acoustic neuroma
oligodendroglioma
meningioma
melanoma
neuroblastoma
retinoblastoma
Virally induced cancers In specific embodiments, a Therapeutic of the invention is used to treat a neoplasm such as a gestational trophoblastic tumor, or testicular germ cell tumor, or cancer of the bladder, pancreas, cervix, lung, liver, ovary, colon or stomach, or adenocarcinoma or a virally induced cancer. In a preferred embodiment, a Therapeutic of the invention is used to treat neuroblastoma or carcinoma of the ovary or stomach. In a more preferred embodiment, a Therapeutic of the invention is used to treat Kaposi's sarcoma or carcinoma of the breast or prostate.

In one aspect of the invention, the Therapeutic is administered in conjunction with other cancer therapy, such as chemotherapy (e.g., treatment with adriamycin, bleomycin, vincristine, vinblastine, doxorubicin and/or Taxol).

The efficacy of a Therapeutic against a particular cancer can be determined by any method known in the art, for example but not limited to, those methods described in Section 5.2 infra.

6.1.1.1. Premalignant Conditions

The Therapeutics of the invention can also be administered to treat premalignant conditions and to prevent progression to a neoplastic or malignant state, including but not limited to those disorders listed in Table 1. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68–79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic of the invention. Such characteristics of a transformed phenotype include morphology changes, looser substratum attachment, loss of contact inhibition, loss of anchorage dependence, protease release, increased sugar transport, decreased serum requirement, expression of fetal antigens, etc.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W. B. Saunders Co., Philadelphia, pp. 112–113, etc.)

In another specific embodiment, a Therapeutic of the invention is administered to a human patient to prevent progression to breast, colon, lung, pancreatic, or uterine cancer, or melanoma or sarcoma.

6.1.2. β-hCG Peptides and Derivatives

In a preferred embodiment of the invention, proteins (e.g., peptides), the amino acid sequence of which consists of a portion of the β-hCG sequence (β-hCG peptides) are used to treat or prevent cancer. In various specific embodiments, the portions of the β-hCG sequence are at least 3, 5, 10, 20, or 30 amino acids. These peptides are preferably β-hCG peptides, or nucleic acids encoding β-hCG peptides, from amino acids 41-54, 45-54, 47-53 and 45-57 (SEQ ID NOS:3–6, respectively) of FIG. 3 (a portion of SEQ ID NO:2). In other embodiments, β-hCG peptides of 41-53, 42-53, 43-53, 44-53, 44-57, 45-53, 46-53, 45-54, 45-55, 45-56, 45-58, 47-54, 47-55, 47-56, 47-58, 48-145, 58-145, 109-119 and 109-145 (SEQ ID NOS:8–24, 7, and 25, respectively) of FIG. 3 (a portion of SEQ ID NO:2) are used to treat or prevent cancer. In another embodiment, a protein is used that (a) comprises a β-hCG amino acid sequence consisting of amino acid numbers 41-54, 45-54, 47-53, 45-57, 45-58, 41-53, 42-53, 43-53, 44-53, 44-57, 45-53, 46-53, 45-54, 45-55, 45-56, 47-54, 47-55, 47-56, 47-58, 48-145, 58-145, 109-119 or 109-145 (SEQ ID NOS:3–6, 18, 8-17, 19-24, 7, and 25, respectively) as depicted in FIG. 3 (a portion of SEQ ID NO:2) and; (b) lacks β-hCG amino acids contiguous to said sequence. Other β-hCG peptides, and nucleic acids encoding these peptides, may have utility in the therapeutic methods of the invention. The utility of β-hCG peptides may be determined by the in vitro and in vivo assays described in Section 5.2 infra or by any other method known in the art.

In specific embodiments, peptides of less than 50, or less than 25, amino acids are provided.

The invention also relates to derivatives, modifications and analogs of β-hCG peptides. In a specific embodiment, a purified derivative of a protein, the amino acid sequence of which protein is selected from the group consisting of amino acid numbers 41-54, 45-54, 47-53, 45-57, 45-58, 41-53, 42-53, 43-53, 44-53, 44-57, 45-53, 46-53, 45-54, 45-55, 45-56, 47-54, 47-55, 47-56, 47-58, 48-145, 58-145, 109-119 or 109-145 (SEQ ID NOS:3–6, 18, 8–17, 19–24, 7 and 25, respectively) as depicted in FIG. 3 (a portion of SEQ ID NO:2) is used to treat or prevent cancer. In one embodiment, β-hCG peptide derivatives can be made by altering the β-hCG peptide sequence by substitutions, additions or deletions that provide for therapeutically effective molecules. Thus, the β-hCG peptide derivatives include peptides containing, as a primary amino acid sequence, all or part of the particular β-hCG peptide sequence including altered sequences in which functionally equivalent amino acid residues are substituted for residues within the sequence resulting in a peptide which is functionally active. For example, one or more amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such β-hCG peptide derivatives can be made either by chemical peptide synthesis or by recombinant production from a nucleic acid encoding the β-hCG peptide which nucleic acid has been mutated. Any technique for mutagenesis known in the art can be used, including but not limited to, chemical mutagenesis, in vitro site-directed mutagenesis (Hutchinson, C., et al., 1978, *J. Biol. Chem* 253:6551), use of TAB® linkers (Pharmacia), etc.

In addition, β-hCG peptides and analogs and derivatives of β-hCG peptides can be chemically synthesized. (See, e.g., Merrifield, 1963, *J. Amer. Chem. Soc.* 85:2149–2156.) For example, peptides can be synthesized by solid phase techniques, cleaved from the resin, and purified by preparative high performance liquid chromatography (e.g., see Creighton, 1983, Proteins, Structures and Molecular Principles, W.H. Freeman and Co., N.Y., pp. 50–60). β-hCG peptides can also be synthesized by use of a peptide synthesizer. The composition of the synthetic peptides may be confirmed by amino acid analysis or sequencing (e.g., the Edman degradation procedure; see Creighton, 1983, Proteins, Structures and Molecular Principles, W.H. Freeman and Co., N.Y., pp. 34–49). Furthermore, it desired, nonclassical amino acids or chemical amino acid analogs can be introduced as a substitution or addition into the β-hCG peptide. Non-classical amino acids include but are not limited to the D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

By way of example but not by way of limitation, peptides of the invention can be chemically synthesized and purified as follows: Peptides can be synthesized by employing the N-α-9-fluorenylmethyloxycarbonyl or Fmoc solid phase peptide synthesis chemistry using a Rainin Symphony Multiplex Peptide Synthesizer. The standard cycle used for coupling of an amino acid to the peptide-resin growing chain generally includes: (1) washing the peptide-resin three times for 30 seconds with N,N-dimethylformamide (DMF); (2) removing the Fmoc protective group on the amino terminus by deprotection with 20% piperidine in DMF by two washes for 15 minutes each, during which process mixing is effected by bubbling nitrogen through the reaction vessel for one second every 10 seconds to prevent peptide-resin settling; (3) washing the peptide-resin three times for 30 seconds with DMF; (4) coupling the amino acid to the peptide resin by addition of equal volumes of a 250 mM solution of the Fmoc derivative of the appropriate amino acid and an activator mix consisting or 400 mM N-methylmorpholine and 250 mM (2-(1H-benzotriazol-1-4))-1,1,3,3-tetramethyluronium hexafluorophosphate (HBTU) in DMF; (5) allowing the solution to mix for 45 minutes; and (6) washing the peptide-resin three times for 30 seconds of DMF. This cycle can be repeated as necessary with the appropriate amino acids in sequence to produce the desired peptide. Exceptions to this cycle program are amino acid couplings predicted to be difficult by nature of their hydrophobicity or predicted inclusion within a helical formation during synthesis. For these situations, the above cycle can be modified by repeating step 4 a second time immediately upon completion of the first 45 minute coupling step to "double couple" the amino acid of interest. Additionally, in the first coupling step in peptide synthesis, the resin can be allowed to swell for more efficient coupling by increasing the time of mixing in the initial DMF washes to three 15 minute washes rather than three 30 second washes. After peptide synthesis, the peptide can be cleaved from the resin as follows: (1) washing the peptide-resin three times for 30 seconds with DMF; (2) removing the Fmoc protective group on the amino terminus by washing two times for 15 minutes in 20% piperdine in DMF; (3) washing the peptide-resin three times for 30 seconds with DMF; and (4) mixing a cleavage cocktail consisting of 95% trifluoroacetic acid (TFA), 2.4% water, 2.4% phenol, and 0.2% triisopropysilane with the peptide-resin for two hours, then filtering the peptide in the cleavage cocktail away from the resin, and precipitating the peptide out of solution by addition of two volumes of ethyl ether. To isolate the peptide, the ether-peptide solution can be allowed to sit at −20° C. for 20 minutes, then centrifuged at 6,000×G for 5 minutes to pellet the peptide, and the peptide can be washed three times with ethyl ether to remove residual cleavage cocktail ingredients. The final peptide product can be purified by reversed phase high pressure liquid chromatography (RP-HPLC) with the primary solvent consisting of 0.1% TFA and the eluting buffer consisting of 80% acetonitrile and 0.1% TFA. The purified peptide can then be lyophilized to a powder.

In a preferred embodiment, the invention provides a peptide with branched amino acids (branched peptide), preferably a branched peptide of amino acids 45-57 (SEQ ID NO:6) with branches occurring at positions 47 and 51, respectively, instead of the Gly and Ala residues normally present. Most preferably, diaminobutyric acid is substituted for the gly and ala residues at positions 47 and 51, respectively, and proline bonded to both diaminobutyric acid residues (45-57 branched) as shown in FIG. 4A.

In other specific embodiments, branched versions of the β-hCG peptides listed hereinabove are provided, e.g., by substituting one or more amino acids within the β-hCG sequence with an amino acid or amino acid analog with a free side chain capable of forming a peptide bond with one or more amino acids (and thus capable of forming a "branch").

Branched peptides may be prepared by any method known in the art for covalently linking any naturally occurring or synthetic amino acid to any naturally occurring or synthetic amino acid in a peptide chain which has a side chain group able to react with the amino or carboxyl group on the amino acids so as to become covalently attached to the peptide chain. In particular, amino acids with a free amino side chain group, such as, but not limited to, diaminobutyric acid, lysine, arginine, ornithine, diaminopropionic acid and citrulline, can be incorporated into a peptide so that an amino acid can form a branch therewith, for example, by forming a peptide bond to the free amino side group, from that residue. Alternatively, amino acids with a free carboxyl side chain group, such as, but not limited to, glutamic acid, aspartic acid and homocitrulline, can be incorporated into the peptide so that an amino acid can form a branch therewith, for example, by forming a peptide bond to the free carboxyl side group, from that residue. The amino acid forming the branch can be linked to a side chain group of an amino acid in the peptide chain by any type of covalent bond, including, but not limited to, peptide bonds, ester bonds and disulfide bonds. In a specific embodiment, amino acids, such as those described above, that are capable of forming a branch point, are substituted for β-hCG residues within a peptide having a β-hCG sequence.

Branched peptides can be prepared by any method known in the art. For example, but not by way of limitation, branched peptides can be prepared as follows: (1) the amino acid to be branched from the main peptide chain can be purchased as an N-α-tert-butyloxycarbonyl (Boc) protected amino acid pentafluorophenyl (Opfp) ester and the residue within the main chain to which this branched amino acid will be attached can be an N-Fmoc-α-γ-diaminobutyric acid; (2) the coupling of the Boc protected amino acid to diaminobutyric acid can be achieved by adding 5 grams of each precursor to a flask containing 150 ml DMF, along with 2.25 ml pyridine and 50 mg dimethylaminopyridine and allowing the solution to mix for 24 hours; (3) the peptide can then be extracted from the 150 ml coupling reaction by mixing the reaction with 400 ml dichlormethane (DCM) and 200 ml 0.12N HCl in a 1 liter separatory funnel, and allowing the phases to separate, saving the bottom aqueous layer and re-extracting the top layer two more times with 200 ml 0.12 N HCl; (4) the solution containing the peptide can be dehydrated by adding 2–5 grams magnesium sulfate, filtering out the magnesium sulfate, and evaporating the remaining solution to a volume of about 2–5 ml; (5) the dipeptide can then be precipitated by addition of ethyl acetate and then 2 volumes of hexanes and then collected by filtration and washed two times with cold hexanes; and (6) the resulting filtrate can be lyophilized to achieve a light powder form of the desired dipeptide. Branched peptides prepared by this method will have a substitution of diaminobutyric acid at the amino acid position which is branched. Branched peptides containing an amino acid or amino acid analog substitution other than diaminobutyric acid can be prepared analogously to the procedure described above, using the N-F-moc coupled form of the amino acid or amino acid analog.

Figure 4B:
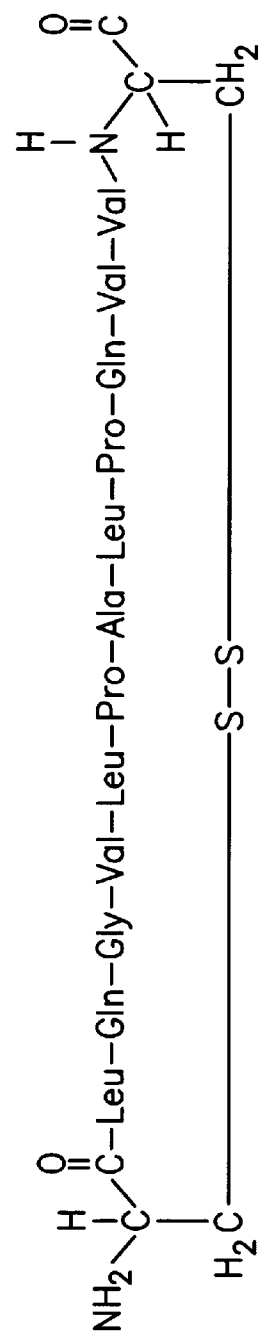

In a preferred embodiment, the peptide is a cyclic peptide, preferably a cyclic peptide of β-hCG amino acids 44-57 (SEQ ID NO:26) with cysteine substituted for valine at position 44 and circularized via a disulfide bond between the cysteine residues at positions 44 and 57 (C[V44C] 45-57) (FIG. 4B). In another preferred embodiment, the peptide is a cyclic branched peptide of β-hCG amino acids 44-57 (SEQ ID NO:12) with cysteine substituted for valine at position 44 and circularized via a disulfide bond between the cysteine residues at positions 44 and 57 and positions 47 and 51 substituted with a diaminobutyric acid residue on which a proline is peptide bonded to its free amino sidechain.

Cyclization can be, for example, but not by way of limitation, via a disulfide bond between two cysteine residues or via an amide linkage. For example, but not by way of limitation, disulfide bridge formation can be achieved by (1) dissolving the purified peptide at a concentration of between 0.1.–0.5 mg/ml in 0.01 M ammonium acetate, pH 7.5; (2) adding to the dissolved peptide 0.01 M potassium ferricyanide dropwise until the solution appears pale yellow in color and allowing this solution to mix for 24 hours; and (3) concentrating the cyclized peptide to 5–10 ml of solution, repurifying the peptide by reverse phase-high pressure liquid chromatography (RP-HPLC) and finally lyophilizing the peptide. In a specific embodiment, in which the peptide does not contain two appropriately situated cysteine residues, cysteine residues can be introduced at the amino-terminus and/or carboxy-terminus and/or internally such that the peptide to be cyclized contains two cysteine residues spaced such that the residues can form a disulfide bridge. Alternatively, a cyclic peptide formed by an amide linkage can be obtained by, for example but not limited to, the following procedure: An allyl protected amino acid, such as aspartate, glutamate, asparagine or glutamine, can be incorporated into the peptide as the first amino acid, and then the remaining amino acids are coupled on. The allyl protective group can be removed by a two hour mixing of the peptide-resin with a solution of tetrakistriphenylphophine palladium (0) in a solution of chloroform containing 5% acetic acid and 2.5% N-methylmorpholine. The peptide resin can be washed three times with 0.5% N,N-diisopropylethylamine (DIEA) and 0.5% sodium diethyldithiocabamate in DMF. The amino terminal Fmoc group on the peptide chain can be removed by two incubations for 15 minutes each in 20% piperdine in DMF, and washed three times with DMF for 30 seconds each. The activator mix, N-methylmorpholine and HBTU in DMF, can be brought onto the column and allowed to couple the free amino terminal end to the carboxyl group generated by removal of the allyl group to cyclize the peptide. The peptide can cleaved from the resin as described in the general description of chemical peptide synthesis above and the peptide purified by reverse phase-high pressure liquid chromatography (RP-HPLC). In a specific embodiment, in which the peptide to be cyclized does not contain an allyl protected amino acid, an allyl protected amino acid can be introduced into the sequence of the peptide, at the amino-terminus, carboxy-terminus or internally, such that the peptide can be cyclized.

β-hCG peptides can also be obtained by recombinant expression techniques. (See, e.g., Sambrook et al., 1989, Molecular Cloning, A Laboratory Manual, Cold Spring Harbor Laboratory, 2d Ed., Cold Spring Harbor, N.Y., Glover, D. M. (ed.), 1985, DNA Cloning: A Practical Approach, MRL Press, Ltd., Oxford, U.K., Vol. I, II). The nucleic acid sequence encoding hCG has been cloned and the sequence determined (see FIG. 3 and Xia, H., 1993, *J. Molecular Endocrinology* Jun. 10; 1993:337–343; Sherman, G. B., 1992, *J. Molecular Endocrinology*, Jun. 6, 1992:951–959; Gieseman, L. K. (ed.), 1991, *Basic and*

*Chemical Endocrinology*, pp. 543–567; Ward et al., 1991, in *Reproduction in Domestic Animals*, 4th ed., P. T. Coppos, ed., pp. 25–80, Academic Press, New York) and can be isolated using well-known techniques in the art, such as screening a library, chemical synthesis, or polymerase chain reaction (PCR).

To recombinantly produce β-hCG peptides, nucleic acid sequence encoding the β-hCG peptide is operatively linked to a promoter such that the β-hCG peptide is produced from said sequence. For example, a vector can be introduced into a cell, within which cell the vector or a portion thereof is expressed, producing the β-hCG peptide. In a preferred embodiment, the nucleic acid is DNA if the source of RNA polymerase is DNA-directed RNA polymerase, but the nucleic acid may also be RNA if the source of polymerase is RNA-directed RNA polymerase or if reverse transcriptase is present in the cell or provided to produce DNA from the RNA. Such a vector can remain episomal or become chromosomally integrated, as long as it can be transcribed to produce the desired RNA. Such vectors can be constructed by recombinant DNA technology methods standard in the art. Vectors can be plasmid, viral, or others known in the art, used for replication and expression in bacterial or mammalian cells. Expression of the sequence encoding the β-hCG peptide can be by any promoter known in the art to act in bacterial or mammalian cells. Such promoters can be inducible or constitutive. Such promoters include, but are not limited to: the SV40 early promoter region (Bernoist and Chambon, 1981, *Nature* 290:304–310), the promoter contained in the 3' long terminal repeat of Rous sarcoma virus (Yamamoto et al., 1980, *Cell* 22:787–797), the HSV-1 (herpes simplex virus-1) thymidine kinase promoter (Wagner et al., 1981, *Proc. Natl. Acad. Sci. USA* 78:1441–1445), the regulatory sequences of the metallothionein gene (Brinster et al., 1982, *Nature* 296:39–42), etc., as well as the following animal transcriptional control regions, which exhibit tissue specificity and have been utilized in transgenic animals: elastase I gene control region which is active in pancreatic acinar cells (Swift et al., 1984, *Cell* 38:639–646; Ornitz et al., 1986, *Cold Spring Harbor Symp. Quant. Biol.* 50:399–409; MacDonald, 1987, Hepatology 7:425–515); insulin gene control region which is active in pancreatic beta cells (Hanahan, 1985, *Nature* 315:115–122), immunoglobulin gene control region which is active in lymphoid cells (Grosschedl et al., 1984, *Cell* 38:647–658; Adames et al., 1985, *Nature* 318:533–538; Alexander et al., 1987, *Mol. Cell. Biol.* 7:1436–1444), mouse mammary tumor virus control region which is active in testicular, breast, lymphoid and mast cells (Leder et al., 1986, *Cell* 45:485–495), albumin gene control region which is active in liver (Pinkert et al., 1987, *Genes and Devel.* 1:268–276), alpha-fetoprotein gene control region which is active in liver (Krumlauf et al., 1985, *Mol. Cell. Biol.* 5:1639–1648; Hammer et al., 1987, *Science* 235:53–58), alpha 1-antitrypsin gene control region which is active in the liver (Kelsey et al., 1987, *Genes and Devel.* 1:161–171), beta-globin gene control region which is active in erythroid cells (Mogram et al., 1985, *Nature* 315:338–340; Kollias et al., 1986, *Cell* 46, 89–94), myelin basic protein gene control region which is active in oligodendrocyte cells in the brain (Readhead et al., 1987, *Cell* 48:703–712), myosin light chain-2 gene control region which is active in skeletal muscle (Sani, 1985, *Nature* 314:283–286), and gonadotropin releasing hormone gene control region which is active in the hypothalamus (Mason et al., 1986, *Science* 234:1372–1378). The promoter element which is operatively linked to the nucleic acid encoding the β-hCG peptide can also be a bacteriophage promoter with the source of the bacteriophage RNA polymerase expressed from a gene for the RNA polymerase on a separate plasmid, e.g., under the control of an inducible promoter, for example, a nucleic acid encoding the β-hCG peptide operatively linked to the T7 RNA polymerase promoter with a separate plasmid encoding the T7 RNA polymerase.

In a less preferred embodiment, peptides can be obtained by proteolysis of hCG followed by purification using standard techniques such as chromatography (e.g., HPLC), electrophoresis, etc.

Also included within the scope of the invention are β-hCG peptide derivatives which are differentially modified during or after synthesis, e.g., by benzylation, glycosylation, acetylation, phosphorylation, amidation, pegylation, derivatization by known protecting/blocking groups, proteolytic cleavage, linkage to an antibody molecule or other cellular ligand, etc. In specific embodiments, the peptides are acetylated at the N-terminus and/or amidated at the C-terminus. Any of numerous chemical modifications may be carried out by known techniques, including but not limited to acetylation, formylation, oxidation, reduction; metabolic synthesis in the presence of tunicamycin, etc.

In another embodiment, the β-hCG peptide derivative is a chimeric, or fusion, protein comprising a functional β-hCG peptide joined at its amino- or carboxy-terminus via a peptide bond to an amino acid sequence of a different protein. In one embodiment, such a chimeric protein is produced by recombinant expression of a nucleic acid encoding the protein (comprising a β-hCG-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

6.1.3. Sources of hCG and β-hCG

Native preparations of hCG and β-hCG can be obtained from a variety of sources. Both hCG and β-hCG are commercially available (e.g., Sigma Chemical Company) and hCG is commercially available in a form suitable for Therapeutic use in humans (e.g., from Fujisawa, Wyeth-Ayerst Laboratories (APL™), Organon, Inc. (Pregnyl™) and Serono Laboratories, Inc. (Profasi™)). The inventors have discovered that different sources of hCG have variable effects on KS tumors and cells in vitro and in vivo; thus, one aspect of the invention relates to assaying preparations of hCG for efficacy in treatment or prevention of cancer. The therapeutic effectiveness of hCG preparations can be tested by the in vitro or in vivo assays described in Section 5.2 infra or by any method known in the art. It is preferable to test the hCG preparation in an in vitro assay, e.g., for effects on tumor cells or transformed cells in culture, or in an animal model, such as mice injected with KS-Y1 or other tumor inducing cells, before testing the preparation in humans.

In a specific embodiment, a preparation comprising hCG is used that contains not only the hCG heterodimer but also peptide fragments thereof, e.g. β chain peptides.

hCG and β-hCG can also be purified, preferably partially purified, from any source known to contain hCG, e.g., urine from pregnant women, using conventional techniques well-known in the art, such as affinity chromatography. For example, antibodies prepared against hCG or β-hCG can be used to prepare an affinity chromatography column which can be used to purify the proteins by well-known techniques (see, e.g., Hudson & May, 1986, *Practical Immunology*, Blackwell Scientific Publications, Oxford, United Kingdom).

The β-hCG-related proteins are preferably prepared by any chemical or enzymatic synthesis method known in the art, as described supra in Section 5.1.2.

6.1.4. Gene Therapy

In a specific embodiment, nucleic acids comprising a sequence encoding β-hCG or a β-hCG peptide, are administered for treatment or prevention of cancer, by way of gene therapy. Gene therapy refers to therapy performed by the administration of a nucleic acid to a subject. In this embodiment of the invention, the nucleic acid produces its encoded protein that mediates a therapeutic effect by preventing or treating cancer. In a preferred embodiment, β-hCG or a β-hCG peptide are provided to treat or prevent Kaposi's sarcoma, or a carcinoma of the breast or prostate. For example, any of the methods for gene therapy available in the art can be used according to the present invention. Exemplary methods are described below.

For general reviews of the methods of gene therapy, see Goldspiel et al., 1993, *Clinical Pharmacy* 12:488–505; Wu and Wu, 1991, *Biotherapy* 3:87–95; Tolstoshev, 1993, *Ann. Rev. Pharmacol. Toxicol.* 32:573–596; Mulligan, 1993, *Science* 260:926–932; and Morgan and Anderson, 1993, *Ann. Rev. Biochem.* 62:191–217; May, 1993, *TIBTECH* 11(5):155–215. Methods commonly known in the art of recombinant DNA technology which can be used are described in Ausubel et al. (eds.): 1993, Current Protocols in Molecular Biology, John Wiley & Sons, NY; and Kriegler, 1990, Gene Transfer and Expression, A Laboratory Manual, Stockton Press, N.Y.

In a preferred aspect, a nucleic acid encoding β-hCG or a β-hCG peptide is part of an expression vector that produces β-hCG or the β-hCG peptide in a suitable host. In particular, such a nucleic acid has a promoter operably linked to the nucleic acid sequence coding for β-hCG or the β-hCG peptide, said promoter being inducible or constitutive, and, optionally, tissue-specific. In another particular embodiment, a nucleic acid molecule is used in which the β-hCG sequences and any other desired sequences are flanked by regions that promote homologous recombination at a desired site in the genome, thus providing for intrachromosomal expression of the hCG nucleic acid (Koller and Smithies, 1989, *Proc. Natl. Acad. Sci. USA* 86:8932–8935; Zijlstra et al., 1989, *Nature* 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then administered to the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the cell or nucleus, e.g., by administering it in linkage to a ligand subject to receptor-mediated endocytosis (see e.g., Wu and Wu, 1987, *J. Biol. Chem.* 262:4429–4432) (which can be used to target cell types specifically expressing the receptors), etc. In a specific embodiment, the nucleic acid can be targeted in vivo for cell specific uptake and expression, by targeting a specific receptor (see, e.g., PCT Publications WO92/06180 dated Apr. 16, 1992 (Wu et al.); WO92/22635 dated Dec. 23, 1992 (Wilson et al.); WO92/20316 dated Nov. 26, 1992 (Findeis et al.); WO93/14188 dated Jul. 22, 1993 (Clarke et al.), WO93/20221 dated Oct. 14, 1993 (Young)). In another embodiment, a nucleic acid-ligand complex can be formed in which the ligand comprises a fusogenic viral peptide to disrupt endosomes, allowing the nucleic acid to avoid lysosomal degradation. Alternatively, the nucleic acid can be introduced intracellularly and incorporated within host cell DNA for expression, by homologous recombination (Koller and Smithies, 1989, *Proc. Natl. Acad. Sci. USA* 86:8932–8935; Zijlstra et al., 1989, *Nature* 342:435–438).

In a specific embodiment, a viral vector that contains the nucleic acid sequence encoding β-hCG or a β-hCG peptide is used. For example, a retroviral vector can be used (see Miller et al., 1993, *Meth. Enzymol.* 217:581–599). These retroviral vectors have been modified to delete retroviral sequences that are not necessary for packaging of the viral genome. Retroviral vectors are maintained in infected cells by integration into genomic sites upon cell division. The nucleic acid to be used in gene therapy is cloned into the vector, which facilitates delivery of the gene into a patient. More detail about retroviral vectors can be found in Boesen et al., 1994, *Biotherapy* 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, *J. Clin. Invest.* 93:644–651; Kiem et al., 1994, *Blood* 83:1467–1473; Salmons and Gunzberg, 1993, *Human Gene Therapy* 4:129–141; and Grossman and Wilson, 1993, *Curr. Opin. in Genetics and Devel.* 3:110–114.

Adenoviruses are other viral vectors that can be used in gene therapy. Adenoviruses are especially attractive vehicles for delivering genes to respiratory epithelia. Adenbviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, *Current Opinion in Genetics and Development* 3:499–503 present a review of adenovirus-based gene therapy. Bout et al., 1994, *Human Gene Therapy* 5:3–10 demonstrated the use of adenovirus vectors to transfer genes to the respiratory epithelia of rhesus monkeys. Other instances of the use of adenoviruses in gene therapy can be found in Rosenfeld et al., 1991, *Science* 252:431–434; Rosenfeld et al., 1992, *Cell* 68:143–155; and Mastrangeli et al., 1993, *J. Clin. Invest.* 91:225–234.

Adeno-associated virus (AAV) has also been proposed for use in gene therapy (Walsh et al., 1993, *Proc. Soc. Exp. Biol. Med.* 204:289–300.) Herpes viruses are other viruses that can also be used.

Another approach to gene therapy, involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including, but not limited to, transfection, electroporation, microinjection, infection with a viral vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, *Meth. Enzymol.* 217:599–618; Cohen et al., 1993, *Meth. Enzymol.* 217:618–644; Cline, 1985, *Pharmac. Ther.* 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells (e.g., keratinocytes) may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

In an embodiment in which recombinant cells are used in gene therapy, a nucleic acid sequence coding for β-hCG or a β-hCG peptide is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

6.2. Demonstration of Therapeutic Utility

The Therapeutics of the invention are preferably tested in vitro, and then in vivo, for the desired therapeutic or prophylactic activity, prior to use in humans.

One embodiment provides a method for screening a preparation comprising a protein, preferably a purified protein, having a sequence of a portion of β-hCG or a derivative, preferably in purified form, of said protein, for anti-cancer activity comprising assaying said preparation for the ability to inhibit the survival or proliferation of malignant cells. In a specific embodiment, the preparation is screened by a method comprising measuring the survival or proliferation of malignant cells, which cells have been contacted with the preparation; and comparing the survival or proliferation of the cells contacted with the preparation with the survival or proliferation of cells not so contacted with the preparation, wherein a lower level of survival or proliferation in said contacted cells indicates that the preparation has anti-cancer activity. In another specific embodiment, the preparation is screened by a method comprising measuring the survival or proliferation of cells from a cell line which is derived from or displays characteristics associated with a malignant disorder, which cells have been contacted with the preparation; and comparing the survival or proliferation in the cells which have been contacted with the preparation with said survival or proliferation in cells not so contacted, wherein a lower level in said contacted cells indicates that the preparation has anti-tumor activity.

Another embodiment provides a method for screening a preparation comprising a protein having a sequence of a portion of β-hCG or a derivative of said protein, for anti-cancer activity comprising assaying said preparation for the ability to convert cells having an abnormal phenotype to a more normal cell phenotype. In a specific embodiment, the preparation is screened by a method comprising assessing the phenotype of cells suspected of being pre-neoplastic in culture, which cells have been contacted with the preparation; and comparing the phenotype in the cells which have been contacted with the preparation with said phenotype in cells not so contacted, wherein a more normal phenotype in said contacted cells indicates that the preparation has anti-cancer activity. In another specific embodiment, the preparation is screened by a method comprising assessing the phenotype of cells from a cell line which is derived from or displays characteristics associated with a pre-malignant disorder, which cells have been contacted with the preparation; and comparing the phenotype in the cells which have been contacted with the preparation with said phenotype in cells not so contacted, wherein a more normal phenotype in said contacted cells indicates that the preparation has anti-cancer activity. Yet another embodiment provides a method for screening a preparation comprising a protein having a sequence of a portion of β-hCG or a derivative of said protein, for activity in treatment or prevention of Kaposi's Sarcoma comprising assaying said preparation for the ability to inhibit Kaposi's Sarcoma cell proliferation or promote Kaposi's Sarcoma cell apoptosis. In a specific embodiment, the preparation is screened by a method comprising measuring proliferation or colony formation in cultured KS Y-1 or KS-SLK cells, which cells have been contacted with the preparation; and comparing the measured proliferation or colony formation in the cells which have been contacted with the preparation with said proliferation or colony formation in cells not so contacted with the preparation, wherein a lower level of proliferation or colony formation in said contacted cells indicates that the preparation has anti-Kaposi's Sarcoma activity. In another specific embodiment, the preparation is screened by a method comprising measuring apoptosis in a Kaposi's Sarcoma tumor in an immunodeficient mouse, which Kaposi's Sarcoma tumors have been induced by injection with KS Y-1 or KS-SLK cells, and which mouse has been exposed to the preparation; and comparing the degree of apoptosis in the tumor of the mouse which has been exposed to the preparation with a tumor in a mouse not so exposed, wherein a higher in level of apoptosis in the tumor of said exposed mouse indicates that the preparation has anti-Kaposi's Sarcoma activity.

For example, in vitro assays which can be used to determine whether administration of a specific Therapeutic is indicated include in vitro cell culture assays in which a patient tissue sample is grown in culture, and exposed to or otherwise administered a Therapeutic, and the effect of such Therapeutic upon the tissue sample is observed. In one embodiment, where the patient has a malignancy, a sample of cells from such malignancy is plated out or grown in culture, and the cells are then exposed to a Therapeutic. A Therapeutic which inhibits survival or growth of the malignant cells is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

In various specific embodiments, in vitro assays can be carried out with representative cells of cell types involved in a patient's disorder, to determine if a Therapeutic has a desired effect upon such cell types.

In another embodiment, cells of a patient tissue sample suspected of being pre-neoplastic are similarly plated out or grown in vitro, and exposed to a Therapeutic. The Therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, *General Virology*, 3d Ed., John Wiley & Sons, New York pp. 436–446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the cell type upon which an effect is desired, according to the present invention.

Specifically, Therapeutics can be tested for efficacy in treatment or prevention of Kaposi's sarcoma by any of the methods relating to Kaposi's sarcoma described in Section 6 infra or in Lunardi-Iskandar et al. (1995, Nature 375:64–68) or by any other method known in the art. Briefly, KS cell lines, KS Y-1 (Ibid.) or KS-SLK (Siegal, B. et al., 1990, Cancer 65:492–498), which will produce malignant tumors in immunodeficient mice, are used to perform in vitro proliferation and clonogenic assays (see, e.g., Lunardi-Iskandar, Y. et al., 1993, *J. Exp. Med.* 177:741–750); methods for performing such assays are well known in the art. A Therapeutic which reduces proliferation or colony formation in the cultured cells can be used in the methods of the invention for treatment or prevention of KS.

Efficacy of a Therapeutic can also be determined by administration of the Therapeutic to immunodeficient mice injected with either the KS-Y-1 or KS-SLK cells, which cause tumor formation in the mice, and assessment of the degree of apoptosis and angiogenesis of tumor cells after treatment with the Therapeutic. Apoptosis is detected by staining fixed tissue samples from the tumor for the presence of cells with DNA fragmentation. For example, this is accomplished by treating tissue slides from formalin-fixed tumors with terminal deoxynucleotide transferase for extension of DNA ends (3' hydroxyl ends) and incorporation of digoxigenin-11-dUTP. Anti-digoxigenin antibody conjugated with the enzyme peroxidase allows detection of apoptotic cells that stain brown whereas viable cells stain blue. An increase in KS tumor cell apoptosis and a decrease in angiogenesis indicates that the Therapeutic has utility in treatment of KS.

The Therapeutic can also be assessed in clinical trials in human patients suffering from KS or any other cancer. To test the efficacy of the Therapeutic in KS patients, either local, i.e. intralesional, or systemic administration of the Therapeutic can be used. Tumors can be examined physically for regression in response to administration of the Therapeutic. Additionally, tissue biopsies can be taken from the tumors, and these tissue samples examined for apoptosis, as described above.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

6.3. Therapeutic Compositions and Methods of Administration

The invention provides methods of treatment and prevention by administration to a subject of an effective amount of a Therapeutic of the invention. The subject is preferably an animal, including but not limited to animals such as cows, pigs, horses, chickens, cats, dogs, etc., and is preferably a mammal, and most preferably human. In a specific embodiment, the subject is a human not afflicted with a cancer which secretes hCG or hCG fragments and, more particularly, not afflicted with Kaposi's Sarcoma.

Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, 1987, *J. Biol. Chem.* 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers. In a preferred embodiment, the pharmaceutical composition of the invention is injected into a KS lesion.

In another embodiment, the Therapeutic can be delivered in a vesicle, in particular a liposome (see Langer, Science 249:1527–1533 (1990); Treat et al., in *Liposomes in the Therapy of Infectious Disease and Cancer*, Lopez-Berestein and Fidler (eds.), Liss, New York, pp. 353–365 (1989); Lopez-Berestein, ibid., pp. 317–327; see generally ibid.)

In yet another embodiment, the Therapeutic can be delivered in a controlled release system. In one embodiment, a pump may be used (see Langer, supra; Sefton, *CRC Crit. Ref. Biomed Eng.* 14:201 (1987); Buchwald et al., *Surgery* 88:507 (1980); Saudek et al., *N. Engl. J. Med.* 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (*Science* 249:1527–1533 (1990)).

In a specific embodiment where the Therapeutic is a nucleic acid encoding a protein Therapeutic, the nucleic acid can be administered by gene therapy methods as described supra Section 5.1.4.

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vivo and/or in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. For treatment of KS, suitable dosages include, but are not limited to, 1,000 to 5,000 I.U. hCG for intralesional injection up to seven days per week and/or 20,000 I.U. intramuscularly or intravenously or subcutaneously) two times per week in human patients. Doses up to 45,000 I.U. per week were also well tolerated by human patients. Predicted suitable doses of β-hCG peptide administered intralesionally include, but are not limited to, 0.1 to 10 micrograms up to and including seven days per week for human patients. For systemic administration, for example but not limited to, intramuscularly, intravenously or subcutaneously, in a specific embodiment, weekly doses of 1 to 1000 micrograms of β-hCG peptide are predicted to be suitable for a human patient. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. optionally associated with such container(s) can be a notice in the form prescribed by a governmental agency regulating the manufacture, use or sale of pharmaceuticals or biological products, which notice reflects approval by the agency of manufacture, use or sale for human administration.

7. EXAMPLE

Effects of hCG and β-hCG Preparations and β-hCG Peptides on Kaposi's Sarcoma

As described herein, we have observed beneficial effects of some preparations of human Chorionic Gonadotropin (hCG) against HIV disease including anti-tumor (Kaposi sarcoma, KS), anti-viral, increase in weight and pro-hematopoiesis effects. Our studies document that the same preparations inhibit KS cell growth in vitro and induce apoptosis in a mouse model. Examples of these effects were also noted in some HIV-positive patients treated with some hCG preparations. The strength of these effects varied among crude hCG preparations, and highly purified hCG did not retain these activities. However, the anti-KS, anti-viral, and pro-hematopoietic effects were mimicked by 2 synthetic peptides of the beta subunit of hCG which we name satellins A1 (amino acid numbers 45-57 (SEQ ID NO:6)) and B (amino acid numbers 109-119 (SEQ ID NO:7)).

7.1. Early Studies of Some hCG Preparations in Patients with HIV-1 Disease

The incidence of KS is greatly increased in HIV-infected persons (Friedman-Kien et al., 1981, *J. Am. Acad. Dermatol.* 5:468–473). Based on experimental studies of the killing effect of some hCG preparations on KS1 cells, clinical trials with some commercially available preparations of hCG given either intralesionally (Hermans et al., 1995, *Cellular and Molecular Biology* 3:357–364; Gill et al., 1996, *NEJM* (in press); Harris, P. J., 1995, *The Lancet* 346:118–119) or systemically to KS patients have shown that cutaneous KS lesions were reduced via cell killing by apoptosis following intralesional inoculation (Lunardi-Iskandar et al., 1995, *Nature* 375:64–68; Hermans et al., 1995, *Cellular and Molecular Biology* 3:357–364; Gill et al., 1996, *NEJM* (in press)) and induced regression of advanced KS disease treated by systemic delivery.

Early clinical and laboratory data from 46 patients (Table 2) treated on two protocols as well as some treated under IRB sanctioned compassionate use, provide instructive examples of the effects of two hCC preparations, APL (Wyeth Ayerst) and Pregnyl (Organon) in patients at various stages of HIV infection. Early clinical experience with relatively low dose intralesional hCG administration for KS documented partial or complete regression of treated lesions including 3 of the first 4 patients in the initial pilot study in Belgium (Hermans et al.,1995, *Cellular and Molecular Biology* 3:357–364) (patients from Belgian study denoted as "PH" in Table 2) as well as a dose dependent effect between 16% (250 IU) and 83% (2,000 IU) in patients reported from California (Gill et al., 1996, *NEJM* (in press)) (patients from California study denoted as "PG" in Table 2), and other cases snowing striking clearance of visceral (lung and gastrointestinal) KS In very advanced disease following systemic therapy with hCG APL or Pregnyl within 1 to 3 months of initiating therapy. in some instances there has been time for long-term evaluation in KS patients and AIDS patients without KS (see below).

AIDS patients treated with hCG therapy were tested for increases in CD4+ T cell levels (in numbers of cells per mm$^3$) and decrease in viral load by one of the following assays for determining viral load: NASBA (Louache, et al., 1992, *Blood* 180:2991–2999; Geller, et al., 1985, *Archs. Path. Lab. Met.* 109:138–145), which has a lower detection limit of 4,000 copies; Roche Amplicor, with a lower detection limit of 200 copies; RT-PCR, with a lower detection limit of 100 copies; or TCID assay in which the infection of PBMCs in co-culture is determined (Popovic et al., 1984, *Science* 204:309–321). Patients were also examined for weight change (in kilograms) and for changes in Kaposi's sarcoma disease. Illustrative examples of the long-term effect of an hCG preparation in advanced AIDS are described below:

As shown in FIGS. 1A and B, the first patient, PH-VE, with cutaneous KS, who enrolled in the formal trial in Belgium and has now been followed for 80 weeks, experienced an increase in CD4+ T cell levels from 100 mm$^3$ to 160 mm$^3$ and a 1.5 log decrease in viral load from 230,000 copies to 11,000 copies by NASBA assay following relatively low dose intralesional injections and subsequent subcutaneous injections for 6 weeks (FIGS. 1A and B). The patient has continued therapy over 72 weeks, and viral load, as measured by RT-PCR, has been maintained at a low level (2,500 to 100 viral copies) and CD4+ T cells have remained stable at 204 mm$^3$ at 68 weeks of hCG therapy (FIG. 1A). A recent KS relapse responded to higher dose hCG treatment (30,000 IU/week).

Figure 1D:
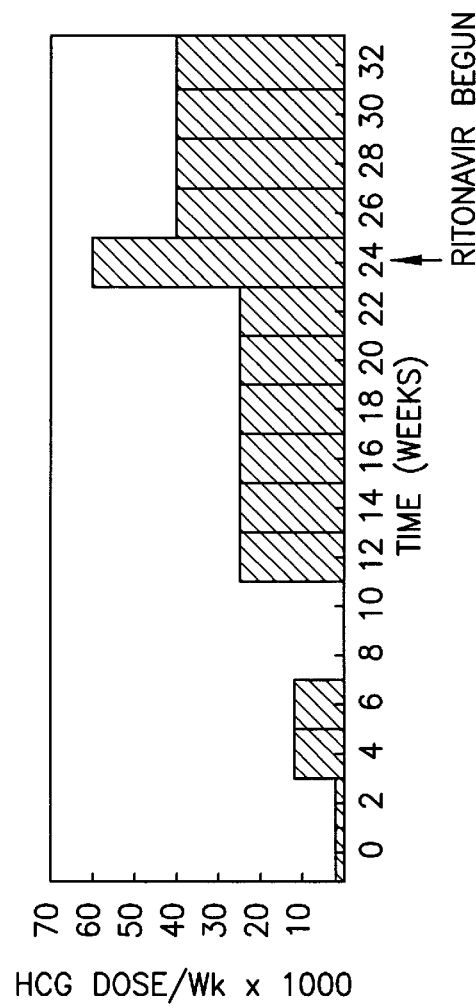

Patient PH-SPBE (FIGS. 1C and D) is illustrative of the synergistic effects of treatment with the hCG preparation followed by antiviral chemotherapy. Foillowing an initial intralesional protocol for 6 weeks, the patient was taken off of hCG therapy for 4 weeks, and then was administered systemic doses of 25,000 IU, followed by 40,000–60,000 IU per week (FIG. 1D). As shown in FIG. 1C, viral load, as measured by NASBA assay, declined from 1,400,000 copies to 700,000 copies and CD4+ T cells stabilized in the mid-100 mm$^3$s. At 22 weeks, Ritonavir therapy was added and subsequent viral load was reduced further and CD4+ T cells rose to over 300 mm$^3$ (FIGS. 1C and D).

Patient PH-OJ (FIGS. 1E and F), who was severely immunosuppressed with CD4+ T cells below 10 mm$^3$, experienced a viral load drop as measured by RT-PCR from 100,000 to 2500 copies after treatment with hCG, but did not experience an increase in CD4+ T cell levels (FIG. 1E). Recently, while on higher doses of hCG (APL), hCG therapy was discontinued because of exacerbation of preexisting cholestasis which required hospitalization.

Of 15 protocol patients from the Belgium trial, an additional 4 had KS responses by ACTGO criteria including several with improved CD4+ T cells and viral load patterns. The non-responders often had very advanced disease and several died during the period of follow-up (Table 2). While viral load and/or CD4+ T cell data were available only for a subset of 29 patients (Table 2), some patients did exhibit increases in CD4+ T cells and some patients also exhibited 1 log or more decreases in viral load (Table 2) without any change in their antiviral therapy.

An additional patients from the Belgium study with advanced disease, some with visceral KS involvement, were treated systemically with higher doses of hCG (15,000 to 30,000 IU) (Table 2). Four have not responded, including 1 who died from opportunistic infection. The remaining 6, however, showed marked responses, including 4 who experienced 75% or more complete regression of visceral KS (Patients PO-DU, PO-GE, PH-JPV, PH-RF), and one (Patient PH-RF) who also demonstrated a decline of viral load from 69,000 copies to less than 4000 copies by NABSA assay (below lower detection limit for the assay).

A recently implemented trial (other "PG" patients in Table 2) employing systemic hCG therapy confirmed a substantial anti-KS effect in 4 of the patients followed for more than 4 months and stabilization of lesions in some patients followed for shorter periods. In one patient (PG-4) on no other antiviral therapy, CD4+ T cell levels rose 10 fold from 47 mm$^3$ to 424 mm$^3$. CD4+ T cell levels in the other patients on anti-virals, including protease inhibitors, were stable or increased. Declines in viral load were noted in several patients, including a 1 log drop in PG-1 (who was on reverse transcriptase inhibitors at enrollment) while stable viral load or demonstrated increases in viral load were noted in other patients (e.g., PG-3 on multiple drugs and PG-15 on no other therapy).

Summarized in Table 2 are the data on 16 patients with paired pre- and post-treatment viral load measurements assayed by either NASBA, Roche Amplicor, or RT-PCR, and 13 patients with paired CD4+ T cell levels and no viral load measurements. In some patients following hCG therapy there were substantial declines in viral load and/or an increase of CD4+ T cells. Since the majority of patients when entered on therapy were also on single or multiple drug anti-viral inhibitors, synergistic effects cannot be ruled out, although some patients showed viral load declines and/or CD4+ T cell increases on hCG alone. Weight gain was recorded in a substantial portion of patients, even some who were in the most advanced stages of HIV infection. Increased appetite and improved sense of well being were also reported. Patient PH-DP with CDC stage B1-HIV disease without KS and with no change in preexisting anti-viral therapy experienced a 2 log reduction in viral load as measure in the TCID assay.

It is important to emphasize that there is potential for selection against obtaining positive "hCG" responses in these treated patients. For example, in some patients with advanced disease, only those who responded to "hCG" therapy at lower doses (less than 15,000 IU total weekly) (e.g., PH-VE, PH-MP) were given further "hCG" therapy, including high doses, while treatment was discontinued in those who did not respond at the lower dose (e.g., PH-LFA, PO-LC, PO-CJP, PO-BO, PO-RB Table 2). Thus, the potential for a higher dose effect was not evaluated in those patients whow did not respond to the lower doses. For example, in patient PH-GA, stabilization of disease was seen at week 6, but complete regression was not recorded until week 14. Responses of patients to dosages of 30,000 to 45,000 IU, particularly the 4 of 5 patients who exhibited regression of KS disease with at least 4 months of follow-up in the initial data from the systemic protocol (35,000 IU/week) encourage the belief that higher doses of some hCG preparations will lead to more consistent beneficial responses. In view of the positive results in these patients, the lack of significant toxicity of these hCG preparations, coupled with the results in monkeys (FIGS. 2A–C) in which a far higher dose was used (considering body weight), it is evident that "non-responders" studied here merit therapy at higher dose level before concluding that any represent true failure to respond.

TABLE 2

Clinical details of patients treated with an hCG preparation

| Patient ID | Duration of Rx (weeks) | Diagnosis | Weekly Dose hCG/IU | CD4/mm³ PreRX | Rx | Viral Load PreRX | Rx | Weight gain Kg | KS response PR = Partial Regression CR = Complete Regression PD = Progressive Disease |
|---|---|---|---|---|---|---|---|---|---|
| PH-VE[a,b] | 80+ | KS-C | 12,500 P / 30,000 P (M20) | 105 | 160(M4) | 230,000 N / 204(M20) | 11,000 | +6 | PR |
| PH-OJ[b] | 31+ | KS-C | 12,500 P | 14 | 3(M4) | 100,000 R | 2,500 R | +3 | PR |
| PH-GF | 18+ | KS-C | 12,500 P | 3 | 35(M2) | 1,100,000 N | 150,000 N | +2 | PR |
| PH-SPBE[b] | 29+ | KS-C | 25,000 PA | 48 | 174(M3) | 1,490,000 N | 770,000 | +1 | PR |
| PH-RF[b] | 12+ | KS-V | 15,000 P | 0 | 17(M3) | 69,000 N | <4000 N | +1 | PR |
| PH-DP[b] | 8+ | No KS | 30,000 P | 517 | NA | 100 T | 1 T (1 mo) | ND | NA |
| PH-JPV | 8+ | KS-V | 15,000 P | <50 | NA | NA | NA | NA | CR |
| PH-LE | 12+* | KS-VC | 30,000 P | <5 | <5(M1) | NA | NA | NA | Stable |
| PH-MP | 24+* | KS-C | 30,000 P | 360 | 505(M3) | NA | NA | +3 | CR |
| PH-GRX[b] | 17+* | KS-C | 12,500 P | 97 | 89(M2) | NA | NA | −3(diet) | PR |
| PH-GA | 12+ | KS-C | 15,000 | 10 | NA | 2,500 R | 500 R | 0 | CR |
| PH-SP[b] | 8+* | KS-VC | 30,000 P | 6 | 5(M1) | NA | NA | 0 | PD |
| PO-FY[b] | 6+* | KS-C | 12,500 P | 180 | 202(M2) | NA | NA | +1.5 | PD |
| PO-GE[b] | 48+* | KS-VC | 15,000 P | 10 | 10(M4) | NA | NA | 0 | CR |
| PO-DU[b] | 37+ | KS-VC | 12,500 P | 5 | 10(M2) | 420,000 N | 300,000 | +2 | Stable |
| PO-LC[b] | 12+ | KS-VC | 12,500 P | 70 | 72(M3) | NA | NA | +1.5 | PD |
| PO-CJP[b] | 6+ | KS-C | 12,500 P | 14 | 14(M1.5) | NA | NA | +1 | PD |
| PO-BO[b] | 6+ | KS-C | 12,500 P | 12 | 12(M1.5) | NA | NA | +1.5 | PD (Died) |
| PO-RB[b] | 4+ | KS-VC | 12,500 P | 50 | 35(1M) | NA | NA | +1 | PD (Died) |
| PG-1[b] | 16+ | KS-C | 35,000 A | 63 | 170(M4) | 75,000 A | 1,700 A | −0.9 | PD |
| PG-3[b,c] | 16+ | KS-C | 35,000 A | 37 | 48(M4) | 52,000 A | 40,000 A | +1.8 | CR |
| PG-4 | 16+ | KS-C | 35,000 A | 47 | 424(M4) | 80,900 A | 55,000 A | +1.4 | Stable |
| PG-6[b,c] | 12+ | KS-C | 35,000 A | 29 | 21(M3) | 62,500 A | 98,000 A | +3.2 | Stable |
| PG-7 | 10+ | KS-C | 30,000 A | 108 | 213 | NA | NA | +4.5 | PR |
| PG-8 | 12 | KS-C | 30,000 A | 787 | 678 | 60.760 A | 22,313 A | +2.3 | PD |
| PG-9 | 11+ | KS-C | 30,000 A | 123 | 218 | NA | NA | −5.0 | Stable |
| PG-10[b] | 12 | KS-C | 30,000 A | 82 | 86 | 25,364 A | 6,777 A | +2.3 | Stable |
| PG-11[b] | 4.5 | KS-C | 30,000 A | 218 | 361 | 661 A | 260 A | +5.4 | Stable |
| PG-12 | 19+ | KS-C | 30,000 A | 22 | 46 | NA | NA | +10.0 | PR |
| PG-15 | 8 | KS-C | 70,000 A | 388 | 483 | 6,162 A | 22,510 A | +1.8 | PD |

*Only patients with CD4+ T-cell and/or viral load data are included. Patients who began protease inhibitors at the beginning or during hCG therapy or who did not comply with hCG therapy (PG-17) are excluded. preRx = before treatment with hCG; Rx = post treatment with hCG. [a]Data on PH-VE are presented in the text reporting stabilization of CD4 levels over 20 months of hCG monotherapy and persistently low viral load by RT-PCR (range 500 to 12,500) with escalating doses of hCG from 15,000 IU (52 weeks) to 30,000 IU per week (Pregnyl) recently which resulted in regression of recurrent cutaneous KS. [b]Patient was on nucleoside/non-nucleoside reverse transcriptase inhibitors when hCG treatment began; [c]Patient was on protease inhibitors when hCG started. The following indicate response of Kaposi's Sarcoma to treatment: PD indicates progressive disease; CR indicates complete response; and PR = Partial response. NA represents data not available. The hCG commercial preparations administered are indicated by P for Pregnyl and A for APL. M represents month from enrollment on protocol. Viral load techniques used are indicated by R for RT-PCR; N for NASBA; T for TCID; A for Roche Amplicor. Under the diagnosis column, KS represents Kaposi sarcoma; KS-V represents KS with visceral involvement; KS-C represents KS with cutaneous lesions only; KS-VC represents KS with both visceral and cutaneous involvement.

Patient Information

A total of 46 patients were available for analysis of whom 30 are included in Table 2 because serial viral load data and/or CD4+ T cell counts were recorded. Twenty-eight patients were treated in Belgium, either on a protocol to investigate intralesional and systemic treatment of cutaneous KS (n=15), or in the pre-clinical phase of that protocol (n=3), or on compassionate use for systemic KS or HIV infection (n=10). The protocol involved intralesional administration of 500 IU hCG (Pregnyl) to 4 lesions for 2 weeks, followed by subcutaneous administration of 2,500 IU hCG (Pregnyl) 5 days per week for 4 to 6 weeks. Additional systemic intramuscular or subcutaneous hCG treatment with either Pregnyl, APL, or Steris (one patient) was provided as ongoing therapy in some patients or as part of compassionate use protocols.

A total of 18 patients were treated in California with at least 1 month of follow-up as part of an ongoing protocol to evaluate systemic hCG therapy for cutaneous KS. These patients received either 5000 IU of APL subcutaneously 7 days per week, 10,000 IU subcutaneously 3 times per week, or 10,000 IU subcutaneously 7 days per week. Five of the systemic cases are not shown because of absent baseline viral load measurements. Five patients with serial viral load measurements started protease inhibitors during the course of hCG therapy and their viral load data is not listed: PG2, who had viral load measurement of 10,496 copies before starting the hCG therapy and a last measurement of 15,542 copies (Roche Amplicor test), started Norvir after hCG; PG5, for whom there was no viral load data started Norvir after hCG; PG-16, had a viral load measurement of 47,931 copies before starting hCG therapy and a last measurement of 370 copies, started Ritonavir after hCG; PG-18, with a viral load of 3673 copies before hCG therapy and a last viral load measurement of 1742 copies, started Crixivan after hCG; PH-SPBE had a viral load of 120,000 copies (NASBA test) compared to the value of 770,000 copies before Ritonavir was added to ongoing hCG treatment; and PH-JPV, had a viral load of 500,000 copies (Roche Amplicor test) before starting hCG therapy and by week 4 of hCG alone, had a viral load of 4,900,000 copies and exhibited undetectable viral load following indinavir (Crixivan) which was added after hCG induced pulmonary response.

Overall 28 patients were on pre-existing, anti-viral therapy (RT inhibitors), 11 were on no anti-virals and 7 were missing information. One patient, PH-RF, was on 3TC therapy before hCG therapy, and despite poor compliance, had an hCG response for visceral KS and viral load, which declined to undetectable on hCG alone.

Thirty-six patients survived the study, 7 (PH-LFA, PH-DD, PH-PJ, PO-BO, PO-PB, PH-JJ, PH-MH) died either from opportunistic infections or multiple organ failure. The vital status of 1 patient is unknown. Two patients, PH-DD and PH-OJ discontinued hCG treatment because of cholestasis. PH-DD was on concomitant anti-mycobacterial therapy which was felt to be a contributing factor. PH-OJ had preexisting cholestasis. When hCG was restarted recently, cholestasis was exacerbated with a marked increase in alkaline phosphatase and rise in bilirubin which required hospitalization. These values declined by 2-fold following discontinuation of hCG. These cases raise the possibility that liver toxicity may be a rare complication of hCG therapy. Among the patients not listed in Table 2, 2 (PG2 and PG5) are on systemic hCG and have exhibited a KS response; 7 (PH-JJ, PH-MH, PH-LG, PH-JPV, PG-16, PG-18) had partial responses; 2 (PO-SC, and PH-LFA) did not respond to hCG or their disease progressed on therapy; 2 (PG-13 and PG-14) are currently in follow-up, but not evaluable; and 4 (PH-PJ, PH-DP, PH-GL, PG17) could not be evaluated or were lost to follow-up. PO-DU experienced stabilization of pulmonary disease and recently developed 2 new cutaneous lesions which responded to radiation therapy without any change in his pulmonary KS. PO-GE experienced complete response to cutaneous and pulmonary KS on hCG alone, PH-RF with gastric KS experienced a marked decline in viral load and a 75% decline and subsequent stabilization of pulmonary KS on hCG, and PH-JPV with pulmonary and gastric KS dramatically improved his pulmonary function test after one month of hCG alone.

7.2. Effects of β-hCG Peptides on Kaposi Sarcoma Cells

Neoplastic KS tumor cells with a characteristic chromosomal abnormality have been reported (Delli-Bovi et al., 1986, Cancer Res. 46:6333–6338; Siegal, et al., 1990, Cancer 65:492–498; Popescu et al., 1995, JNCI 88:450–454) and provide a model system for studying the in vitro effects of hCG. In our prior studies employing immune deficient mice injected with KS tumor cells, some commercial preparations of native hCG killed KS tumor cells in vivo by inducing apoptosis and inhibiting angiogenesis. In vitro tumor cell colonies are also suppressed in clonogenic assays by the hCG preparations (Lunardi-Iskandar et al., 1995, Nature 375:64–68; Nakamura et al., 1988, Science 242:426–430; Ensoli et al., 1989, Science 243:223–226; Salahuddin et al., 1988, Science 242:430–433; Masood, et al., 1984, AIDS Res. Hum. Retroviruses 10:969–976). In the current study, experiments were performed to investigate whether certain β-hCG peptides had with the anti-KS effect of native hCG both in vitro in clonogenic assays on cultured KS Y-1 cells and in vivo in KS tumors induced in nude mice.

Briefly, the KS Y-1 cells were obtained from mononuclear cells isolated from pleural effusion of an AIDS patient with KS involving the lungs. After the depletion of T lymphocytes, monocytes/macrophages and fibroblasts by the cytotoxicity method, using monoclonal antibodies against CD2, CD3, CD4, CD8, CD10 and CD14 membrane antigens and baby rabbit complement, the cells were cultured in the absence of exogenous growth factors to select for transformed cells. Immunological characterization of the KS Y-1 cells showed that CD34, CD31 and endoglin were expressed. Clonogenic assays were performed by seeding the KS Y-1 or KS-SLK cells in methylcellulose (0.8%, v/v), incubating the cells for 10 days in the presence or absence of the hCG, β-hCG or β-hCG peptide preparation and then counting the number of well-formed colonies of triplicate wells formed after seeding with $5 \times 10^4$ cells.

As shown in FIG. 2A, the peptides (50 nmoles/ml) with the strongest anti-viral effects (peptides of amino acids 45-57 (SEQ ID NO:6), cyclic 44-57, with cysteine substituted at position 44 (SEQ ID NO:26) and 109-119 (SEQ ID NO:7)) also had the strongest anti-tumor effects (anti-KS) on 2 KS neoplastic cell lines. It is notable that the purified hCG heterodimer (CR127 2 nmoles/ml) was again inactive as it was in the HIV assays. There was no anti-KS effect with the pure α- and β-chains and the following peptides were tested and showed little or no inhibition in clonogenic assays: α-hCG peptide 88-92; and the β-hCG peptides of amino acids 6-16, 7-40, 34-49, 38-57, 57-93, 74-95, 100-110 123-145, and 134-144. Scrambled β-hCG peptides 45-57 and 109-119 showed little inhibition. Peptides were obtained from Bachem, Calif., Rockville Peptides Inc or generously provided by Dr. N. Ambulos of the University of Maryland (Medical Center) at Baltimore.

The effects of the peptides on KS tumor cells were also evaluated in vivo in the mouse model. To induce KS tumors in the mice, 1×10⁶/ml KS Y-1 cells in 50 μl PBS or saline were injected subcutaneously into immunodeficient mice (beige-XID-BNX mice). After one week, tumors ranged in size from 2×3 mm to 3×5 mm. Methods for detection of apoptosis (from tissue biopsies) were used, as described in Lunardi-Iskandar, Y. et al.(1995, *Nature* 375:64–68). Briefly, the samples were stained in situ for the presence of cells with DNA fragmentation. Tissue slides from formalin-fixed tumors were treated with terminal deoxynucleotide transferase for extension of DNA ends (hydroxyl 3') and incorporation of digoxigenin-11-dUTP according to the manufacturer's instructions (Oncor, Gaithersburg, Md.). Anti-digoxigenin antibody conjugated with the enzyme peroxidase allowed detection of apoptotic cells that stain brown whereas viable cells stain blue.

Figure 2B:
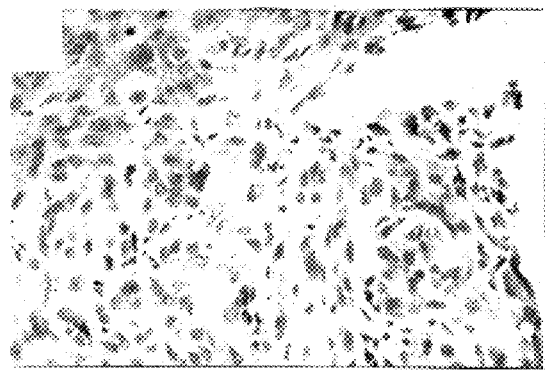
Figure 2C:
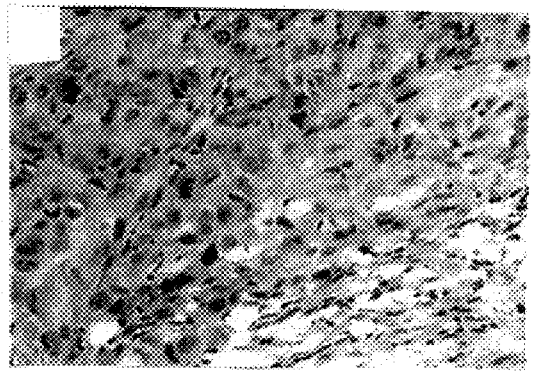
Figure 2D:
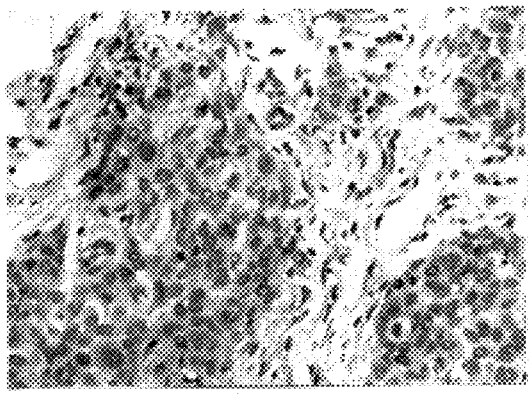
Figure 2E:
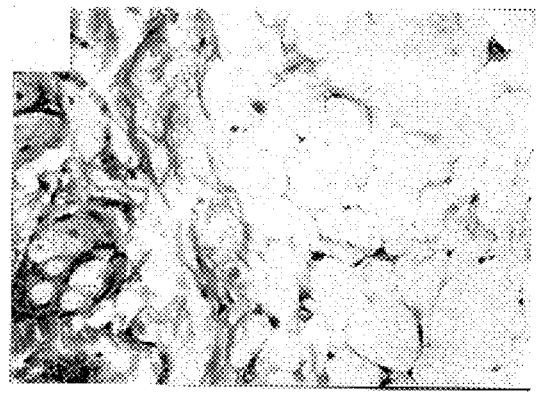

Shown in FIGS. 2B–E are representative examples of the effects of hCG and the β-hCG peptides on KS Y-1 tumors in mice. One week after injection with the tumor cells, the mice were treated with crude hCG (APL, Wyeth Ayerst) or with β-chain peptides 45-57 (SEQ ID NO:6) and cyclic 44-57 [Cys44] (SEQ ID NO:26). FIGS. 2B–E show hematoxylin and eosin staining of thin tissue sections of KS Y-1 induced tumors. Compared to the frequent mitotic activity in the controls (FIG. 2B), there is evidence of extensive cell death in the tumors of the animals treated with the β-hCG peptides which are comparable to the findings in animals treated with active hCG preparations (FIGS. 2C–E). Some other overlapping β-chain peptides had slight activity (compared to β-hCG peptides 45-57 (SEQ ID NO:6) and 109-119 (SEQ ID NO:7)). These include peptides which form the β-core (β-hCG peptides 6-40 and 55-90) and one which overlapped satellin A1 (β-hCG peptide 38-57). The a subunit peptide was inactive as were numerous other β-chain peptides such as β-hCG 6-16, 34-49, 57-93, 74-95, 93-100, 100-110, 12:3-145, and 134-144.

Figure 2F:
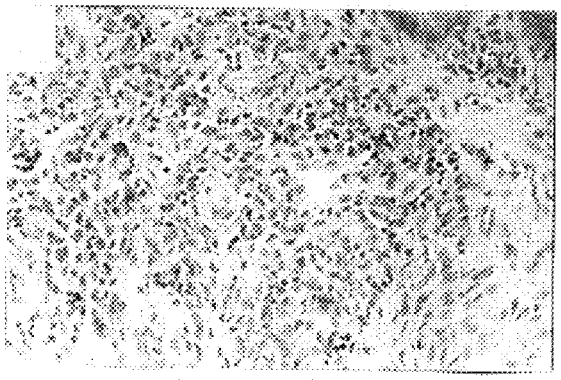
Figure 2G:
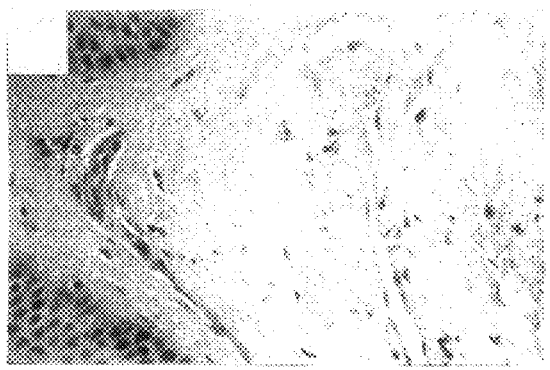
Figure 2H:
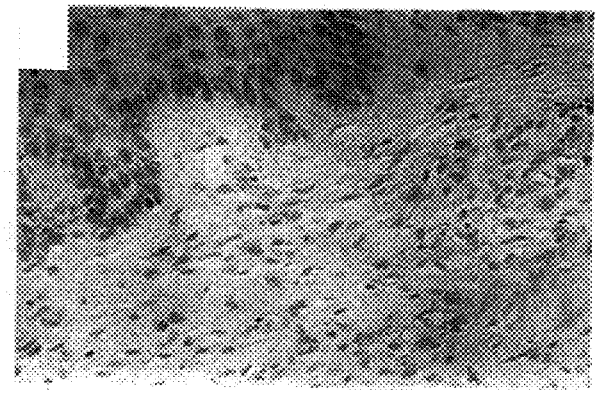

As noted above, some AIDS-KS patients treated by intralesional or systemic injection of some preparations of hCG experience regression of tumor lesions of the skin as well as visceral KS (Hermans et al., 1995, *Cellular and Molecular Biology* 3:357–364; Gill et al., 1996, NEJM (in press)). Patients receiving these preparations showed macroscopic regression and flattening of KS lesions. In situ immunostaining specific for apoptosis detection in tumor biopsies showed evidence of apoptosis and/or, histologically, complete absence of the KS tumor after 2–3 weeks of hCG therapy as shown in FIGS. 2F, G and H, similar to that seen in the experimental mouse model with the active β-hCG peptides. In control KS tumors treated with diluent only or untreated KS tumor tissues (not shown), there was little evidence of cell death (FIG. 2F).

7.3. Discussion

The discovery of an anti-KS effect of the pregnancy hormone, hCG, was observed in vivo in pregnant Bg-nude mice who did not develop KS as did their male litter mates inoculated at the same time with the KS Y-1 KS tumor line. This observation led to clinical trials of intralesional therapy for KS which documented responses in 83% of treated lesions at the higher dose schedule (Gill, P. S., et al., 1996, submitted). We show herein that some patients treated intralesionally with hCG for KS were noted to have a reduction in viral load and in vitro and in vivo animal model data show that some hCG preparations, partially purified β-hCG, and the active β-hCG fragments (β-hCG peptides 45-57 and 109-119) have anti-KS effects.

We found considerable anti-KS activity with the native partially purified whole β-chain, but recombinant β-hCG (purified) had little or no effect. We suspect that the lower molecular weight species may retain the effect and that some purification procedure may not eliminate those species.

The native hCG and native β-chain preparations available for clinical use are not homogenous and may be contaminated with one or more other active molecules. In this respect, it is noteworthy that though the effects of some preparations of hCG described here were obtained with two different commercial sources of hCG (APL and Pregnyl), one was usually more active (APL) at lower concentrations than any other preparation, although it too varied from lot to lot as detected in the immunodeficient mouse KS system (data not shown) despite the fact that we used identical amounts (International Units) as assessed by the manufacturer's standard bioassays for the conventional use of hCG. The differences in activities of commercial preparations might be explained by variation in the amount of β-hCG fragments. This could be the consequence of different methods of preparation or different sources of human urine. For example, free β-hCG is more abundant in the earliest weeks of pregnancy. Consequently, we initiated studies with a variety of synthetic peptides, and our results show that all the in vitro activities of the preparations of native hCG are mimicked by the β-hCG peptides 45-57, and 109-119 but not other β- or α-peptides or scrambled 45-57 peptide. Thus, we suggest that β-hCG contains structural motifs that produce effects which probably work by mechanisms which differ from those currently known for hCG. We suspect that β-hCG fragments have biological functions quite distinct from the conventional effects of the heterodimer. The structural features of hCG (Lapthorn, A. J., et al., 1994, *Nature* 369:455–461) and appearance in very early pregnancy (Fan, C., et al., 1987, *J. Clin. Endo. Metab.* 64:313–318) combined with some of our observed effects of the β-chain peptides on Kaposi's Sarcoma tumors involving induction of apoptosis (Lunardi-Iskandar, Y., et al., 1995, *Nature* 375:64–68), suggest that the structural similarity to some growth factors may be important and might also be relevant to the hematopoietic growth promoting and anti-viral effects observed here. In view of the evidence that the α subunits are needed for binding to the hCG receptor, we are uncertain how the β peptides initiate these effects. Thus, whether the effects we have observed (anti-viral, anti-tumor, anti-wasting and pro-hematopoietic) are mediated by known hCG receptors is unknown. Given that the mechanism of action of these hCG fragments is likely to involve pathways distinctive from normal hCG hormonal pathways, it is proposed that these active peptides represent a new class of active molecules which we named Satellins. The first members of this class are Satellin A for the active moiety from the β-hCG peptide 45-57 and Satellin B for the β-hCG peptide 109-119.

In laboratory tests, KS cells were killed and regression occurred of transplanted KS tumors in mice (Lunardi-Iskandar, Y., et al., 1995, *Nature* 375:64–68). A recent clinical study of escalating dose by intralesional injection of hCG (APL, Wyeth Ayerst) for cutaneous KS skin lesions, demonstrated tumor regression in a dose-dependent manner with 8% responding at the lowest dose (250 IU three times per week) and 83% at the highest intralesional dose (2000 IU three times per week) (Gill, P. S., et al., 1996, submitted). It is also noteworthy that regression of visceral lesions occurred in 2 KS patients with advanced KS (Hermans, P., et al., 1995, *AIDS. Res. Hum. Retroviruses* S:96).

The clinical data reported herein confirms many of the beneficial effects. observed in the laboratory preclinical studies. As discussed above, some preparations of hCG induced partial or complete regression of KS lesions in patients treated intralesionally when the hCG (APL, Wyeth Ayerst) was used at dose levels of 250 to 2000 IU three times per week.

The intrinsic variability of native hCG preparations led to the discovery that certain β-hCG peptides (satellins) reproduce the anti viral and anti KS effects in vitro as well as the anti-KS effect in mice with transplanted KS tumors.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

---

What is claimed is:

1. A method of treating cancer or inhibiting growth of cancer cells in a subject in need of such treatment or inhibition comprising administering to the subject a therapeutically effective amount of a purified protein or peptide comprising a β-hCG segment consisting of β-hCG 45-57 (SEQ ID NO:6), and lacking β-hCG amino acids contiguous to β-hCG 45-57.

2. A method of treating cancer or inhibiting growth of cancer cells in a subject in need of such treatment or inhibition comprising administering to the subject a therapeutically effective amount of a purified protein or peptide comprising a circularized β-hCG segment consisting of β-hCG 45-57 (SEQ ID NO:6), and lacking β-hCG amino acids contiguous to β-hCG 45-57.

3. A method of treating cancer or inhibiting growth of cancer cells in a subject in need of such treatment or inhibition comprising administering to the subject a therapeutically effective amount of a purified protein or peptide comprising a branched β-hCG segment consisting of β-hCG 45-57 (SEQ ID NO:6), and lacking β-hCG amino acids contiguous to β-hCG 45-57.

4. A method of treating cancer or inhibiting growth of cancer cells in a subject in need of such treatment or inhibition comprising administering to the subject a therapeutically effective amount of a purified protein or peptide comprising a circularized and branched β-hCG segment consisting of β-hCG 45-57 (SEQ ID NO:6), and lacking β-hCG amino acids contiguous to β-hCG 45-57.

5. A method of treating cancer or inhibiting growth of cancer cells in a subject in need of such treatment or inhibition comprising administering to the subject a therapeutically effective amount of a purified protein or peptide comprising a β-hCG segment consisting of an amino acid sequence selected from the group consisting of β-hCG amino acid numbers 41-54, 45–54, 47-53, 45-57, 45-58, 41-53, 42-53, 43-53, 44-53, 44-57, 45-53, 46-53, 45-55, 45-56, 47-54, 47-55, 47-56, and 47-58 (SEQ ID NOS: 3–6, 18, 8–14, 16, 17, 19–22, 7, and 25, respectively), and lacking β-hCG amino acids contiguous to said sequence, said protein or peptide being active to treat cancer or inhibit growth of cancer cells.

6. A method of treating cancer or inhibiting growth of cancer cells in a subject in need of such treatment or inhibition comprising administering to the subject a therapeutically effective amount of a purified protein or peptide comprising a circularized β-hCG segment consisting of an amino acid sequence selected from the group consisting of β-hCG amino acid numbers 41-54, 45-54, 47-53, 45-57, 45-58, 41-53, 42-53, 43-53, 44-53, 44–57, 45-53, 46-53, 45-55, 45-56, 47-54, 47-55, 47-56, and 47-58 (SEQ ID NOS: 3–6, 18, 8–14, 16, 17, 19–22, 7, and 25, respectively), and lacking β-hCG amino acids contiguous to said sequence, said protein or peptide being active to treat cancer or inhibit growth of cancer cells.

7. A method of treating cancer or inhibiting growth of cancer cells in a subject in need of such treatment or inhibition comprising administering to the subject a therapeutically effective amount of a purified protein or peptide comprising a branched β-hCG segment consisting of an amino acid sequence selected from the group consisting of β-hCG amino acid numbers 41-54, 45-54, 47-53, 45-57, 45-58, 41-53, 42-53, 43-53, 44-53, 44-57, 45-53, 46-53, 45-55, 45-56, 47-54, 47-55, 47-56, and 47-58 (SEQ ID NOS: 3–6, 18, 8–14, 16, 17, 19–22, 7, and 25, respectively), and lacking β-hCG amino acids contiguous to said sequence, in which one or more residues in said sequence are substituted by an amino acid or amino acid analog having a side chain with an amino or carboxyl group, said amino or carboxyl group forming a peptide bond with a second sequence of one or more amino acids, said protein or peptide being active to treat cancer or inhibit growth of cancer cells.

8. A method of treating cancer or inhibiting growth of cancer cells in a subject in need of such treatment or inhibition comprising administering to the subject a therapeutically effective amount of a purified protein or peptide comprising a circularized and branched β-hCG segment consisting of an amino acid sequence selected from the group consisting of β-hCG amino acid numbers 41-54, 45-54, 47-53, 45-57, 45-58, 41-53, 42-53, 43-53, 44-53, 44-57, 45-53, 46-53, 45-55, 45-56, 47-54, 47-55, 47-56, 47-58, and 47-58 (SEQ ID NOS: 3–6, 18, 8–14, 16, 17, 19–22, 7, and 25, respectively), and lacking β-hCG amino acids contiguous to said sequence, in which one or more residues in said sequence are substituted by an amino acid or amino acid analog having a side chain with an amino or carboxyl group, said amino or carboxyl group forming a peptide bond with a second sequence of one or more amino acids, said protein or peptide being active to treat cancer or inhibit growth of cancer cells.

9. A method of treating cancer or inhibiting growth of cancer cells in a subject in need of such treatment or inhibition comprising administering to the subject a therapeutically effective amount of a purified protein or peptide comprising a circularized β-hCG segment consisting of an amino acid sequence selected from the group consisting of β-hCG amino acid numbers 41-54, 45-54, 47-53, 45-57, 45-58, 41-53, 42-53, 43-53, 44-53, 44-57, 45-53, 46-53, 45-55, 45-56, 47-54, 47-55, 47-56, and 47-58 (SEQ ID NOS: 3–6, 18, 8–14, 16, 17, 19–22, 7, and 25, respectively), and lacking β-hCG amino acids contiguous to said sequence, wherein the segment has at least two cysteine residues, optionally wherein:
 (a) at least one cysteine residue has been inserted between two non-cysteine amino acid residues;
 (b) at least one cysteine residue has been coupled at an end of the segment; or
 (c) at least one non-cysteine amino acid residue has been replaced by a cysteine residue;
wherein two cysteine residues are coupled together by a disulfide bond, said protein or peptide being active to treat cancer or inhibit growth of cancer cells.

10. A method of treating cancer or inhibiting growth of cancer cells in a subject in need of such treatment or inhibition comprising administering to the subject a therapeutically effective amount of a purified protein or peptide comprising a branched β-hCG segment consisting of an amino acid sequence selected from the group consisting of β-hCG amino acid numbers 41-54, 45-54, 47-53, 45-57, 45-58, 41-53, 42-53, 43-53, 44-53, 44-57, 45-53, 46-53, 45-55, 45-56, 47-54, 47-55, 47-56, and 47-58 (SEQ ID NOS: 3–6, 18, 8–14, 16, 17, 19–22, 7, and 25, respectively), and lacking β-hCG amino acids contiguous to said sequence, in which one or more residues in said sequence are substituted by an amino acid or amino acid analog having a side chain with an amino or carboxyl group, said amino or carboxyl group forming a peptide bond with a second sequence of one or more amino acids, wherein the segment has at least two cysteine residues, optionally wherein:
 (a) at least one cysteine residue has been inserted between two non-cysteine amino acid residues;
 (b) at least one cysteine residue has been coupled at an end of the segment; or
 (c) at least one non-cysteine amino acid residue has been replaced by a cysteine residue;
wherein two cysteine residues are coupled together by a disulfide bond, said protein or peptide being active to treat cancer or inhibit growth of cancer cells.

11. The method of claim 7 in which the segment includes positions 47 and 51 and the residues at positions 47 and 51 are each substituted by a diaminobutyric acid residue and the side chain amino group of said diaminobutyric acid residue is peptide bonded to a proline residue.

12. The method of claim 8 in which the segment includes positions 47 and 51 and the residues at positions 47 and 51 are each substituted by a diaminobutyric acid residue and the side chain amino group of said diaminobutyric acid residue is peptide bonded to a proline residue.

13. The method of claim 7 in which the one or more residues are each substituted by a diaminobutyric acid residue and the side chain amino group of said diaminobutyric acid residue is peptide bonded to a sequence of one or more proline residues.

14. The method of claim 8 in which the one or more residues are each substituted by a diaminobutyric acid residue and the side chain amino group of said diaminobutyric acid residue is peptide bonded to a sequence of one or more proline residues.

15. The method of claim 1 in which the protein, peptide or segment is N-acetylated and/or has a C-terminal amide.

16. The method of claim 6 in which the protein, peptide or segment is N-acetylated and/or has a C-terminal amide.

17. The method of claim 7 in which the protein, peptide or segment is N-acetylated and/or has a C-terminal amide.

18. The method of claim 8 in which the protein, peptide or segment is N-acetylated and/or has a C-terminal amide.

19. The method of claim 1 further comprising administering chemotherapy to the subject.

20. The method of claim 6 further comprising administering chemotherapy to the subject.

21. The method of claim 7 further comprising administering chemotherapy to the subject.

22. The method of claim 8 further comprising administering chemotherapy to the subject.

23. The method of claim 1 in which the cancer is selected from the group consisting of Kaposi's Sarcoma, breast cancer and prostate cancer.

24. The method of claim 6 in which the cancer is selected from the group consisting of Kaposi's Sarcoma, breast cancer and prostate cancer.

25. The method of claim 7 in which the cancer is selected from the group consisting of Kaposi's Sarcoma, breast cancer and prostate cancer.

26. The method of claim 8 in which the cancer is selected from the group consisting of Kaposi's Sarcoma, breast cancer and prostate cancer.

27. The method of claim 23 in which the protein or peptide is administered by intralesional and/or intramuscular injection.

28. The method of claim 24 in which the protein or peptide is administered by intralesional and/or intramuscular injection.

29. The method of claim 25 in which the protein or peptide is administered by intralesional and/or intramuscular injection.

30. The method of claim 26 in which the protein or peptide is administered by intralesional and/or intramuscular injection.

31. The method of claim 1 in which the segment contains one or more D-amino acids or non-classical amino acids.

32. The method of claim 6 in which the segment contains one or more D-amino acids or non-classical amino acids.

33. The method of claim 7 in which the segment contains one or more D-amino acids or non-classical amino acids.

34. The method of claim 8 in which the segment contains one or more D-amino acids or non-classical amino acids.

35. A method of treating cancer or inhibiting growth of cancer cells in a subject in need of such treatment or inhibition comprising administering to the subject an amount of a purified protein or peptide consisting of the amino acid sequence Leu-Gln-Gly-Val-Leu-Pro-Ala-Leu-Pro-Gln-Val-Val-Cys (SEQ ID NO:6).

36. A method of treating cancer or inhibiting growth of cancer cells in a subject in need of such treatment or inhibition comprising administering to the subject an amount of a purified protein or peptide consisting of the amino acid sequence Leu-Gln-Dab(Pro)-Val-Leu-Pro-Dab(Pro)-Leu-Pro-Gln-Val-Val-Cys, where "Dab" represents diaminobutyric acid, and Dab(Pro) indicates a proline peptide-bonded to the amino side chain of Dab.

37. A method of treating cancer or inhibiting growth of cancer cells in a subject in need of such treatment of inhibition comprising administering to the subject an amount of a purified protein or peptide consisting of the amino acid sequence Cys-Leu-Gln-Gly-Val-Leu-Pro-Ala-Leu-Pro-Gln-Val-Val-Cys (SEQ ID NO:26), wherein the terminal Cys residues are linked together by a disulfide bond.

38. A method of treating cancer or inhibiting growth of cancer cells in a subject in need of such treatment or inhibition comprising administering to the subject an amount of a purified protein or peptide consisting of the amino acid sequence Thr-Cys-Asp-Asp-Pro-Arg-Phe-Gln-Asp-Ser-Ser (SEQ ID NO: 7).

* * * * *